US010687777B2

(12) United States Patent
Dascal et al.

(10) Patent No.: US 10,687,777 B2
(45) Date of Patent: Jun. 23, 2020

(54) VASCULAR DATA PROCESSING AND IMAGE REGISTRATION SYSTEMS, METHODS, AND APPARATUSES

(71) Applicant: LightLab Imaging, Inc., Westford, MA (US)

(72) Inventors: Lorina Dascal, Haifa (IL); Itai Winkler, Yoqne'am (IL); Stavit Cohen, Kerem-Maharal (IL); Amit Cohen, Binyamina (IL); Desmond C. Adler, Concord, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 51 days.

(21) Appl. No.: 15/911,749

(22) Filed: Mar. 5, 2018

(65) Prior Publication Data
US 2018/0192983 A1 Jul. 12, 2018

Related U.S. Application Data

(60) Continuation of application No. 15/058,338, filed on Mar. 2, 2016, now Pat. No. 9,907,527, which is a
(Continued)

(51) Int. Cl.
*A61B 6/00* (2006.01)
*G06T 7/11* (2017.01)
(Continued)

(52) U.S. Cl.
CPC .......... *A61B 6/5258* (2013.01); *A61B 5/0035* (2013.01); *A61B 5/0066* (2013.01);
(Continued)

(58) Field of Classification Search
CPC ..... A61B 6/5258; A61B 6/487; A61B 6/4417; A61B 6/463; A61B 6/12; A61B 6/481;
(Continued)

(56) References Cited

U.S. PATENT DOCUMENTS 4,769,850 A * 9/1988 Itoh ...................... G06K 9/4609
382/132
5,321,501 A 6/1994 Swanson et al.
(Continued)

FOREIGN PATENT DOCUMENTS

JP 2010-526556 8/2010
JP 2012-223346 11/2012
(Continued)

OTHER PUBLICATIONS

Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.
(Continued)

*Primary Examiner* — John B Strege

(74) *Attorney, Agent, or Firm* — K&L Gates LLP

(57) ABSTRACT

In part, the invention relates to processing, tracking and registering angiography images and elements in such images relative to images from an intravascular imaging modality such as, for example, optical coherence tomography (OCT). Registration between such imaging modalities is facilitated by tracking of a marker of the intravascular imaging probe performed on the angiography images obtained during a pullback. Further, detecting and tracking vessel centerlines is used to perform a continuous registration between OCT and angiography images in one embodiment.

19 Claims, 31 Drawing Sheets

Related U.S. Application Data division of application No. 13/798,018, filed on Mar. 12, 2013, now Pat. No. 9,351,698.

(51) Int. Cl.

| | | |
|---|---|---|
| *A61B 6/12* | (2006.01) | |
| *A61B 8/12* | (2006.01) | |
| *A61B 5/00* | (2006.01) | |
| *G06T 7/00* | (2017.01) | |
| *A61B 8/00* | (2006.01) | |
| *A61B 6/03* | (2006.01) | |
| *A61B 5/055* | (2006.01) | |
| *A61B 90/00* | (2016.01) | |
| *A61M 25/10* | (2013.01) | |

(52) U.S. Cl.
CPC .......... *A61B 5/0073* (2013.01); *A61B 5/0084* (2013.01); *A61B 6/12* (2013.01); *A61B 6/4417* (2013.01); *A61B 6/463* (2013.01); *A61B 6/481* (2013.01); *A61B 6/487* (2013.01); *A61B 6/504* (2013.01); *A61B 6/5247* (2013.01); *A61B 8/12* (2013.01); *G06T 7/0012* (2013.01); *G06T 7/11* (2017.01); *A61B 5/055* (2013.01); *A61B 6/032* (2013.01); *A61B 6/507* (2013.01); *A61B 8/4245* (2013.01); *A61B 8/565* (2013.01); *A61B 2090/364* (2016.02); *A61B 2090/3735* (2016.02); *A61B 2090/3966* (2016.02); *A61M 25/104* (2013.01); *A61M 2025/105* (2013.01); *G06T 2207/10101* (2013.01); *G06T 2207/30101* (2013.01); *G06T 2207/30204* (2013.01)

(58) Field of Classification Search
CPC ... A61B 6/5247; A61B 5/0066; A61B 5/0035; A61B 5/0073; A61B 5/0084; A61B 8/12; A61B 8/4245; A61B 8/565; A61B 2090/3966; A61B 2090/364; A61B 2090/3735; A61B 6/032; A61B 6/507; A61B 5/055; G06T 7/11; G06T 7/0012; G06T 2207/30101; G06T 2207/30204; G06T 2207/10101; A61M 25/104; A61M 2025/105

See application file for complete search history.

(56) References Cited

U.S. PATENT DOCUMENTS

| | | | |
|---|---|---|---|
| 5,459,570 A | 10/1995 | Swanson et al. | |
| 5,465,147 A | 11/1995 | Swanson | |
| 5,509,093 A | 4/1996 | Miller et al. | |
| 5,586,201 A | 12/1996 | Whiting et al. | |
| 5,619,368 A | 4/1997 | Swanson | |
| 5,715,827 A | 2/1998 | Corl et al. | |
| 5,748,598 A | 5/1998 | Swanson et al. | |
| 5,784,352 A | 7/1998 | Swanson et al. | |
| 5,822,391 A | 10/1998 | Whitting | |
| 5,917,859 A | 6/1999 | Yamasaki et al. | |
| 5,956,355 A | 9/1999 | Swanson et al. | |
| 6,111,645 A | 8/2000 | Tearney et al. | |
| 6,134,003 A | 10/2000 | Tearney et al. | |
| 6,148,095 A * | 11/2000 | Prause | G06T 17/00 382/131 |
| 6,160,826 A | 12/2000 | Swanson et al. | |
| 6,191,862 B1 | 2/2001 | Swanson et al. | |
| 6,195,445 B1 | 2/2001 | Jolly et al. | |
| 6,282,011 B1 | 8/2001 | Tearney et al. | |
| 6,302,875 B1 | 10/2001 | Makower et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,565,514 B2 | 5/2003 | Svanerudh et al. | |
| 6,570,659 B2 | 5/2003 | Schmitt | |
| 6,706,004 B2 | 3/2004 | Tearney et al. | |
| 6,728,566 B1 | 4/2004 | Subramanyan et al. | |
| 6,731,973 B2 | 5/2004 | Voith | |
| 6,879,851 B2 | 4/2005 | McNamara et al. | |
| 6,891,984 B2 | 5/2005 | Petersen et al. | |
| 6,937,696 B1 | 8/2005 | Mostafavi | |
| 6,973,202 B2 | 12/2005 | Mostafavi | |
| 7,068,831 B2 | 6/2006 | Florent et al. | |
| 7,134,994 B2 | 11/2006 | Alpert et al. | |
| 7,191,100 B2 | 3/2007 | Mostafavi | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,301,644 B2 | 11/2007 | Knighton et al. | |
| 7,321,677 B2 | 1/2008 | Evron et al. | |
| 7,414,779 B2 | 8/2008 | Huber et al. | |
| 7,415,049 B2 | 8/2008 | Flanders et al. | |
| RE40,608 E | 12/2008 | Glover et al. | |
| 7,593,559 B2 | 9/2009 | Toth et al. | |
| 7,625,366 B2 | 12/2009 | Atlas | |
| 7,697,972 B2 | 4/2010 | Verard et al. | |
| 7,729,746 B2 | 6/2010 | Redel et al. | |
| 7,742,797 B2 | 6/2010 | Redel et al. | |
| 7,792,342 B2 | 9/2010 | Barbu et al. | |
| 7,813,609 B2 | 10/2010 | Petersen et al. | |
| 7,848,791 B2 | 12/2010 | Schmitt et al. | |
| 7,869,663 B2 | 1/2011 | Buckland et al. | |
| 7,872,759 B2 | 1/2011 | Tearney et al. | |
| 7,916,387 B2 | 3/2011 | Schmitt et al. | |
| 7,918,793 B2 | 4/2011 | Altmann et al. | |
| 7,925,327 B2 | 4/2011 | Weese | |
| 7,930,014 B2 | 4/2011 | Huennekens et al. | |
| 7,935,060 B2 | 5/2011 | Schmitt et al. | |
| 7,988,633 B2 | 8/2011 | Hossack et al. | |
| 7,991,105 B2 | 8/2011 | Mielekamp et al. | |
| 8,029,447 B2 | 10/2011 | Kanz et al. | |
| 8,116,605 B2 | 2/2012 | Petersen et al. | |
| 8,206,374 B2 | 6/2012 | Duane et al. | |
| 8,206,377 B2 | 6/2012 | Petroff | |
| 8,259,303 B2 | 9/2012 | Johnson et al. | |
| 8,290,228 B2 | 10/2012 | Cohen et al. | |
| 8,298,147 B2 | 10/2012 | Huennekens et al. | |
| 8,325,419 B2 | 12/2012 | Schmitt | |
| 8,351,665 B2 | 1/2013 | Tearney et al. | |
| 8,358,461 B2 | 1/2013 | Huber et al. | |
| 8,412,312 B2 | 4/2013 | Judell et al. | |
| 8,423,121 B2 | 4/2013 | Wang et al. | |
| 8,449,468 B2 | 5/2013 | Petersen et al. | |
| 8,457,375 B2 | 6/2013 | Rieber et al. | |
| 8,457,440 B1 | 6/2013 | Johnson | |
| 8,463,007 B2 | 6/2013 | Steinberg et al. | |
| 8,478,387 B2 | 7/2013 | Xu | |
| 8,503,844 B2 | 8/2013 | Petersen et al. | |
| 8,542,900 B2 | 9/2013 | Tolkowsky et al. | |
| 8,556,820 B2 | 10/2013 | Alpert et al. | |
| 8,562,537 B2 | 10/2013 | Alpert et al. | |
| 8,571,639 B2 | 10/2013 | Mostafavi | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,670,603 B2 | 3/2014 | Tolkowsky et al. | |
| 8,693,756 B2 | 4/2014 | Tolkowsky et al. | |
| 8,700,130 B2 | 4/2014 | Iddan et al. | |
| 8,781,193 B2 | 7/2014 | Steinberg et al. | |
| 8,855,744 B2 | 10/2014 | Tolkowsky et al. | |
| 8,909,323 B2 | 12/2014 | Baumgart | |
| 8,913,084 B2 | 12/2014 | Chen et al. | |
| 2002/0161351 A1 | 10/2002 | Samson et al. | |
| 2003/0163048 A1 | 8/2003 | Rafter et al. | |
| 2004/0006277 A1 | 1/2004 | Langenhove et al. | |
| 2005/0043614 A1 | 2/2005 | Huizenga et al. | |
| 2005/0201662 A1 | 9/2005 | Petersen et al. | |
| 2006/0050958 A1 | 3/2006 | Okada et al. | |

(56) References Cited

U.S. PATENT DOCUMENTS

| | | | |
|---|---|---|---|
| 2006/0058643 A1* | 3/2006 | Florent | A61B 6/481 600/423 |
| 2006/0095065 A1 | 5/2006 | Tanimura et al. | |
| 2007/0024617 A1 | 2/2007 | Poole | |
| 2007/0066890 A1 | 3/2007 | Maschke | |
| 2007/0135803 A1 | 6/2007 | Belson | |
| 2008/0221439 A1 | 9/2008 | Iddan et al. | |
| 2008/0221440 A1 | 9/2008 | Iddan et al. | |
| 2008/0221442 A1 | 9/2008 | Tolkowsky et al. | |
| 2009/0174931 A1 | 7/2009 | Huber et al. | |
| 2009/0306520 A1 | 12/2009 | Schmitt et al. | |
| 2010/0076320 A1 | 3/2010 | Petersen et al. | |
| 2010/0094124 A1 | 4/2010 | Schoonenberg et al. | |
| 2010/0157041 A1 | 6/2010 | Klaiman et al. | |
| 2010/0160764 A1 | 6/2010 | Steinberg et al. | |
| 2010/0160773 A1 | 6/2010 | Cohen et al. | |
| 2010/0161022 A1 | 6/2010 | Tolkowsky et al. | |
| 2010/0161023 A1 | 6/2010 | Cohen et al. | |
| 2010/0172556 A1 | 7/2010 | Cohen et al. | |
| 2010/0191102 A1 | 7/2010 | Steinberg et al. | |
| 2010/0222671 A1 | 9/2010 | Cohen et al. | |
| 2010/0228076 A1 | 9/2010 | Blank et al. | |
| 2010/0290693 A1 | 11/2010 | Cohen et al. | |
| 2011/0071404 A1 | 3/2011 | Schmitt et al. | |
| 2011/0101207 A1 | 5/2011 | Schmitt | |
| 2011/0157686 A1 | 6/2011 | Huber et al. | |
| 2011/0190586 A1 | 8/2011 | Kemp | |
| 2011/0228280 A1 | 9/2011 | Schmitt et al. | |
| 2011/0298922 A1 | 12/2011 | Horovitz et al. | |
| 2011/0319752 A1 | 12/2011 | Steinberg et al. | |
| 2012/0004529 A1 | 1/2012 | Tolkowsky et al. | |
| 2012/0004537 A1 | 1/2012 | Tolkowsky et al. | |
| 2012/0029339 A1 | 2/2012 | Cohen et al. | |
| 2012/0310081 A1 | 6/2012 | Adler et al. | |
| 2012/0238869 A1 | 9/2012 | Schmitt et al. | |
| 2012/0250028 A1 | 10/2012 | Schmitt et al. | |
| 2012/0277570 A1 | 11/2012 | Todor et al. | |
| 2012/0300215 A1 | 11/2012 | Johnson et al. | |
| 2012/0300216 A1 | 11/2012 | Johnson et al. | |
| 2013/0010303 A1 | 1/2013 | Petersen et al. | |
| 2013/0012811 A1 | 1/2013 | Schmitt et al. | |
| 2013/0023761 A1 | 1/2013 | Petroff | |
| 2013/0051728 A1 | 2/2013 | Petroff | |
| 2013/0072805 A1 | 3/2013 | Schmitt et al. | |
| 2013/0077888 A1 | 3/2013 | Meyers et al. | |
| 2013/0123616 A1 | 5/2013 | Merritt et al. | |
| 2013/0310698 A1 | 11/2013 | Judell et al. | |
| 2014/0094660 A1 | 4/2014 | Tolkowsky et al. | |
| 2014/0094689 A1 | 4/2014 | Cohen et al. | |
| 2014/0094691 A1 | 4/2014 | Steinberg et al. | |
| 2014/0094692 A1 | 4/2014 | Tolkowsky et al. | |
| 2014/0094693 A1 | 4/2014 | Cohen et al. | |
| 2014/0100451 A1 | 4/2014 | Tolkowsky et al. | |
| 2014/0107479 A1 | 4/2014 | Klaiman et al. | |
| 2014/0114184 A1 | 4/2014 | Klaiman et al. | |
| 2014/0114185 A1 | 4/2014 | Tolkowsky et al. | |
| 2015/0250438 A1 | 9/2015 | Bozkaya et al. | |

FOREIGN PATENT DOCUMENTS

| | | |
|---|---|---|
| WO | 2012176191 | 12/2012 |
| WO | 2013175472 | 11/2013 |
| WO | 2014002095 | 3/2014 |

OTHER PUBLICATIONS

International Search Report and Written Opinion mailed from the International Searching Authority dated Jun. 27, 2014 for International Application No. PCT/US2013/030623 (17 pages).

Dave Fornell, "The Advantages and Disadvantages of OCT vs. IVUS", Diagnostic and Interventional Cardiology, May 18, 2011, pp. 1-4.

Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

Perez-Rovira et al., "Deformable Registration of Retinal Fluorescein Angiogram Sequences Using Vasculature Structures", 32nd Annual Conf. of IEEE EMBS, 2010, pp. 4383-4386.

Japanese Office Action dated Jul. 2, 2019, Application No. 2018-152711.

* cited by examiner

VASCULAR DATA PROCESSING AND IMAGE REGISTRATION SYSTEMS, METHODS, AND APPARATUSES

CROSS-REFERENCE TO RELATED APPLICATIONS

This application is a continuation of U.S. patent application Ser. No. 15/058,338, filed on Mar. 2, 2016, which is a divisional of U.S. patent application Ser. No. 13/798,018, filed on Mar. 12, 2013, now U.S. Pat. No. 9,351,698, the entire disclosures of which are incorporated by reference herein.

FIELD OF THE INVENTION

In part, the invention relates generally to the field of vascular system and peripheral vascular system imaging and data collection.

BACKGROUND OF THE INVENTION

Interventional cardiologists incorporate a variety of diagnostic tools during catheterization procedures in order to plan, guide, and assess therapies. Fluoroscopy is generally used to perform angiographic imaging of blood vessels. In turn, such blood vessel imaging is used by physicians to diagnose, locate and treat blood vessel disease during interventions such as bypass surgery or stent placement. Intravascular imaging technologies such as optical coherence tomography (OCT) and acoustic technologies such as intravascular ultrasound (IVUS) and others are also valuable tools that can be used in lieu of or in combination with fluoroscopy to obtain high-resolution data regarding the condition of the blood vessels for a given subject.

Fractional flow reserve (FFR) can also be used to evaluate a blood vessel during imaging and angiography. Intravascular OCT, IVUS, and FFR are invasive catheter-based systems that collect optical, ultrasound, and pressure data, respectively, from inside blood vessels or with respect to a sample of interest. Angiography is a noninvasive x-ray imaging method that collects data from outside the body during injection of a radio-opaque contrast fluid.

Intravascular optical coherence tomography is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease.

Given the complexity of the various technologies described above and the associated complexity of the datasets each of them generate, performing co-registration between two image-based technologies such as OCT and angiography is time consuming. As a result, challenges regarding real time co-registration of intravascular image data and angiography image data remain. Some co-registration techniques depend heavily on user interaction. Unfortunately, taxing an operator with significant user interaction during co-registrations such as requiring manually matching corresponding points in images, a long waiting period for the algorithms to return a co-registration, and finally verifying the results, makes such approaches impractical in many clinical scenarios. In addition, other approaches use data from asynchronous or third party controlled sources which results in timing irregularities. In addition, since contrast agents, such as dyes, are used with some intravascular imaging modalities that interfere with other noninvasive imaging modalities, imaging artifacts and errors can result which interfere with co-registration between such modalities.

Accordingly, a need therefore exists to address one or more of the challenges identified above relating to intravascular imaging and angiography imaging. Embodiments of the invention address these challenges and others.

SUMMARY OF THE INVENTION

One embodiment of the invention relates to methods for registration between two imaging modalities such as angiography and OCT. One embodiment of the invention relates to one or more methods for performing co-registration between angiography images and the OCT images.

One embodiment of the invention relates to a method for performing detection of stationary marker band on a frame without a contrast agent such as a dye and with a contrast agent. In addition, one embodiment of the invention further provides for tracking of such a marker band as it moves through a lumen of a blood vessel such that it is tracked on subsequent pullback frames, including tracking from a frame without contrast agent to a frame with contrast agent.

In one embodiment, the time period to register between about 20 and 100 frames of angiography image frames and between about 100 and about 1500 frames of OCT image frames ranges from about 2 seconds to about 30 seconds. In one embodiment, registration of angiography image data and OCT image data obtained during an OCT pullback are co-registered in less than about 10 seconds. In one embodiment, the pullback of a data collection probe ranges from about 4 to about 10 seconds. In one embodiment, frames of angiography are obtained in real time using a frame grabber. The frames of angiography data are grabbed in a synchronized manner with the OCT image data frames obtained as a result of the pullback.

In one embodiment, a co-registration method co-registers an OCT frames of image data obtained during the imaging of a pullback with frames of angiography data obtained during such a pullback within a registration time period of about 3 to about 5 seconds.

In one embodiment, the invention relates to an image data processing system that includes a frame grabber, an OCT system configured to perform imaging during pullback of a data collection probe having a marker through a blood vessel and generate time stamped OCT image data with respect to the blood vessel, one or more computing devices, and a user interface, wherein the frame grabber is configured to obtain time stamped frames of angiography image data with respect to the blood vessel.

In one embodiment, video capture of angiography image data occurs on the OCT system. In one embodiment, a user manually designates a marker band on an angiography image. In one embodiment, the designated marker band is on an angiography image without contrast agent. In one embodiment, the user interface includes a longitudinal OCT image panel, a cross-sectional OCT image panel, one or more controls, and an angiography image panel. In one embodiment, the user interface includes a register control or button that causes the computing devices to execute one or more software modules configured to co-register the OCT image data and the angiography image data. In one embodiment, the time stamps are used to give a first-order match between angiography frames and their corresponding OCT frames, such that for every OCT frame, the closest angiography frame can be located, and vice versa. In addition, time-stamped events, such as pullback start and stop, are also recorded to assist the co-registration process.

In one embodiment, a cursor or other identifier on the angiography image denotes the location of the OCT catheter reference markers coinciding with the OCT pullback frame selected. In one embodiment, a cursor or other identifier can also denote the user-selected proximal and distal reference frames within which MLA has been calculated, and denote the mean diameter of the blood vessel. Scrolling through the co-registered OCT and angiography images can be controlled via the OCT L-mode or a cursor on angiography frame as a remote controller or as part of the user interface.

In one embodiment, a filter kernel such as a convolution matrix is implemented as a matrix including rows and columns and elements configured to perform image processing for performing intensifying, sharpening, pattern identification, detection, tracking and other image processing tasks. The filter kernel can be used in various preprocessing and other processing stages to perform image processing on angiography image data or other image data.

In one embodiment, the invention relates to a processor-based method of displaying an angiographic and an intravascular representation of a blood vessel. The method includes generating a set of OCT image data in response to distance measurements of a blood vessel using an optical coherence tomography system, the set comprising a plurality of cross-sectional image at a plurality of positions along the blood vessel; generating a set of angiography image data, the set comprising a plurality of two dimensional images at a plurality of positions along the blood vessel; and co-registering the angiography images and OCT images based on one or more of a time stamp, a relationship between time stamps, matching of a feature in an OCT image with a feature in an angiography image, and determining a centerline for the blood vessel and using the centerline to co-register the OCT images and angiography images.

In one aspect, the invention relates to a processor-based method of displaying an angiographic and an intravascular representation of a blood vessel. The method includes generating a set of optical coherence tomography image data in response to distance measurements of the blood vessel obtained during a pullback of a probe through the blood vessel using an optical coherence tomography system, the set of OCT image data comprising a plurality of cross-sectional image at a plurality of positions along the blood vessel; generating a set of angiography image data using an angiography system during the pullback of the probe through the blood vessel using an optical coherence tomography system, the set of angiography image data comprising a plurality of two-dimensional images obtained at different points in time during the pullback; displaying a first panel comprising a first longitudinal view of the blood vessel generated using the OCT image data; and displaying a second panel comprising a frame of the angiography image data identifying the blood vessel using one or more points in the frame and a vessel centerline passing through the one or more points.

In one embodiment, the method further includes co-registering the OCT image data and the angiography data using vessel centerlines to create a continuous registration of a tracked marker, wherein the tracked marker is disposed on an OCT data collection probe. In one embodiment, the method further includes co-registering the OCT image data and the angiography data such that selecting a point along the vessel centerline through a user interface changes a frame identifier in the first longitudinal view. In one embodiment, the method further includes using pullback speed or pullback length to perform an iterative search to reject candidates for the tracked marker based on the possible locations for such markers based upon the pullback length and/or pullback speed.

In one embodiment, the vessel centerline is generated using a shortest path technique and a plurality of processing steps from a Dijkstra algorithm. In one embodiment, the method further includes the step of removing a guide catheter image from one or more frames of angiography data using superposition of an intensity profile. In one embodiment, the vessel centerline is generated using path information generated from one or more angiography frames substantially in the absence of contrast solution. In one embodiment, the method 1 further includes generating a confidence score for each detection and co-registration between angiography data and optical coherence tomography data.

In one aspect, the invention relates to a method of detecting an intravascular probe marker comprising obtaining a first frame of angiography image data that is substantially free of contrast agent image data and includes the intravascular probe marker; obtaining a second frame of angiography image data that comprises contrast agent image data in the vicinity of the intravascular probe marker; and detecting the intravascular probe marker in the first frame and the second frame.

In one embodiment, the method further includes the steps of applying an image processing transform to the second frame to remove or modify a feature in the second frame and increasing an intensity of a plurality of pixels, the plurality of pixels comprising a guidewire image in the second frame. In one embodiment, the method further includes the step of generating an average intensity value for a plurality of images and subtracting the average intensity from the first or second frame. In one embodiment, the method includes applying a bottom hat operator to the second frame and applying a morphological close operation.

In one embodiment, detecting the intravascular probe marker comprises filtering candidate markers comprising pixels in the first frame and the second frame by applying a multiscale Laplacian of Gaussian operator on the first frame and the second frame and performing a non-maxima suppression process to identify blobs having a relative maximum in a neighborhood of pixels.

In one embodiment, the method further includes the step of generating a guidewire-based potential function by applying a Euclidian distance transform on a binary image. The method can also include applying an exponent to a negative fractional power times the distance transform to compute the potential function. In one embodiment, the method further includes determining a plurality of geodesic distances based on the guidewire-based potential using a fast marching method.

In one embodiment, the method further includes removing a shadow from the first frame and the second frame, increasing a contrast level of a guidewire on one of the first frame or second frame, and performing a morphological image reconstruction for each marker candidate. In one embodiment, the method includes processing the plurality of pullback frames using a Hessian-based vesselness filter; and tracking the intravascular probe marker from one of the first frame or the second frame through the plurality of pullback frames to all the pullback frames using template matching.

In one embodiment, the method further includes tracking the intravascular probe marker through a plurality of frames obtained during the pullback using a Viterbi dynamic programming method.

In one aspect, the invention relates to a processor-based method of co-registering angiographic image data and intravascular image data obtained during a pullback through a blood vessel. The method includes storing a plurality of frames of optical coherence tomography data in memory; storing a plurality of frames of angiography image data in memory; processing the plurality of frames of angiography image data such that one or more shadows are substantially reduced; detecting a catheter in the plurality of frames of angiography image data; removing the detected catheter in the plurality of frames of angiography image data; generating a vessel centerline for the plurality of frames of angiography image data; detecting a probe marker in the plurality of frames of angiography image data; tracking a position of the probe marker along one or more vessel centerlines; and co-registering the plurality of frames of angiography image data and the plurality of frames of optical coherence tomography data using the tracked position.

In one embodiment, the method includes generating a score indicative of a level of confidence in co-registration between a frame of angiography image data and a frame of the optical coherence tomography data. In one embodiment, the method includes removing the detected catheter is performed using superposition of an intensity profile generated based on a sampling of regions of the detected catheter.

In one embodiment, the step of co-registering the plurality of frames of angiography image data and the plurality of frames of optical coherence tomography data comprises generating a co-registration table, using a computing device, the co-registration table comprising angiography image frames, a plurality of per frame OCT time stamps, a plurality of per frame angiography time stamps, and optical coherence tomography image frames. In one embodiment, the method further includes displaying a stent representation in an OCT image and an angiography image in a user interface using the co-registration table and a computing device.

In one embodiment, the method further includes identifying a side branch in one or more OCT images or angiography images using the co-registration table and a user interface configured to display the side branch. In one embodiment, the method further includes to set the spacing of the frames of OCT data based on the co-registration table to adjust for pullback speed changes and to display a longitudinal view in a user interface based on the spacing.

BRIEF DESCRIPTION OF THE DRAWINGS

The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION

Figure 1:
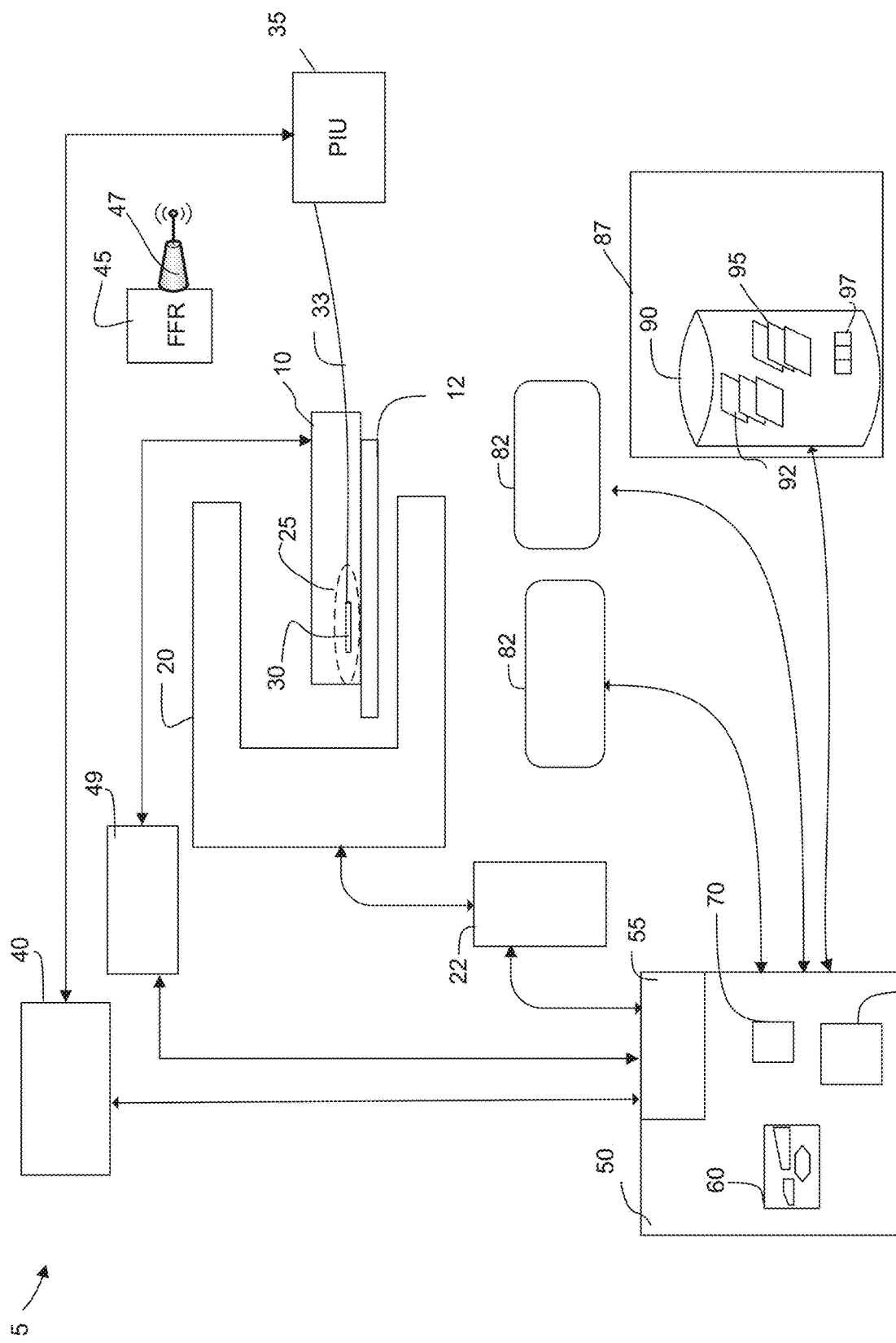
FIG. 1 shows a schematic diagram of an angiography and intravascular imaging and data collection system in accordance with an illustrative embodiment of the invention.

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention; rather, the scope of the present invention is defined by the claims.

As described above, there are challenges relating to vascular and peripheral vascular diagnostic systems such as challenges relating to implementing co-registration for multiple imaging technologies such as angiography, OCT, and IVUS. In part, the invention relates to various systems, components thereof, and methods for use in a catheter lab or other facility to collect data from a subject and help improve upon one or more of these limitations. The data collected is typically related to the patient's cardiovascular or peripheral vascular system and can include image data, pressure data, heart rate, and other types of data as described herein.

In addition, in one embodiment image data is collected using optical coherence tomography probes and other related OCT components. In one embodiment image data is collected using IVUS probes and other related IVUS components. In addition, in one embodiment pressure data is collected using FFR probes and other related FFR components. In addition, in one embodiment EKG, heart rate, and other subject data is collected using electrodes and other related components.

In addition, some embodiments of the invention are suitable for handling multiple imaging modalities. Thus, in part, the invention relates to a multimodal diagnostic system and components thereof configured to co-register one or more of the following OCT, IVUS, FFR, and angiography. OCT data and image processing results can be used to improve the processing of frames of angiography images by providing input into angiography specific software modules.

IVUS imaging features can also be incorporated into the data collection probe used in conjunction with collecting the angiography data in one embodiment. Further, FFR pressure measurements can also be performed using suitable pressure transducers and probes. In one embodiment, the FFR data collecting probes or transducers can include a wireless transmitter and employ a wireless receiver to receive and communicate FFR data to the server. Comparison and co-registration of OCT and/or IVUS images with angiographic images are achieved by interfacing the system with an angiography device or a hospital data network wherein the angiographic data is stored.

In one embodiment, a user such as a clinician interacts with a workstation or server having an associated user interface for displaying images of a subject's blood vessels from a top down, longitudinal cross-section, or a cross-section substantially parallel to the longitudinal axis of the vessel. The co-registration process can include various steps and image processing and feature detection software modules. In one embodiment, a user or a system activates intravascular imaging while acquiring angiographic images. The blood vessel being imaged intravascularly and the imaging catheter can be displayed as part of a graphic user interface. The boundary of the lumen of the vessel can be identified in each intravascular and angiography image and related to each other to maintain the same vessel segment on different views.

Since the imaging catheter is introduced by a guidewire, the guidewire can be used as an anchor path and to provide directional information such as what endpoint is distal and what endpoint is proximal in the relevant imaging segment. In one embodiment, a guide catheter slides along the guidewire to position a probe tip having one or more imaging devices in the blood vessel. In one embodiment, the angiographic image data is processed such that the guide catheter is removed from the image after it has been identified.

In one embodiment, one or more software modules are used to generate and track a vessel centerline for a given frame of angiography data. In one embodiment, a vessel centerline also referred to herein as a centerline is a model or simulation that is generated based on an iteratively evaluation of each candidate subset of a frame of angiographic data for marker bands associated with the optical or acoustic sensor or other imaging or data collecting sensor introduced during the angiographic data collection. In one embodiment, a dynamic program software module such as a software module implementing one or more steps of the Viterbi algorithm can be used to track the marker bands. In one embodiment, the Viterbi algorithm is used for radiopaque marker tracking. The creation and tracking of the centerlines are typically handled by other algorithms or combinations thereof. In one embodiment, the vessel centerlines are generated by a combination of algorithms or processes for finding the shortest path between two far points such as a fast marching algorithm on the Hessian image and a modified Dijkstra algorithm.

FIG. 1 shows a system 5 which includes various data collection subsystems suitable for collecting data or detecting a feature of or sensing a condition of or otherwise diagnosing a subject 10. In one embodiment, the subject is disposed upon a suitable support 12 such as table bed to chair or other suitable support. Typically, the subject 10 is the human or another animal having a particular region of interest 25.

Figure 2A:
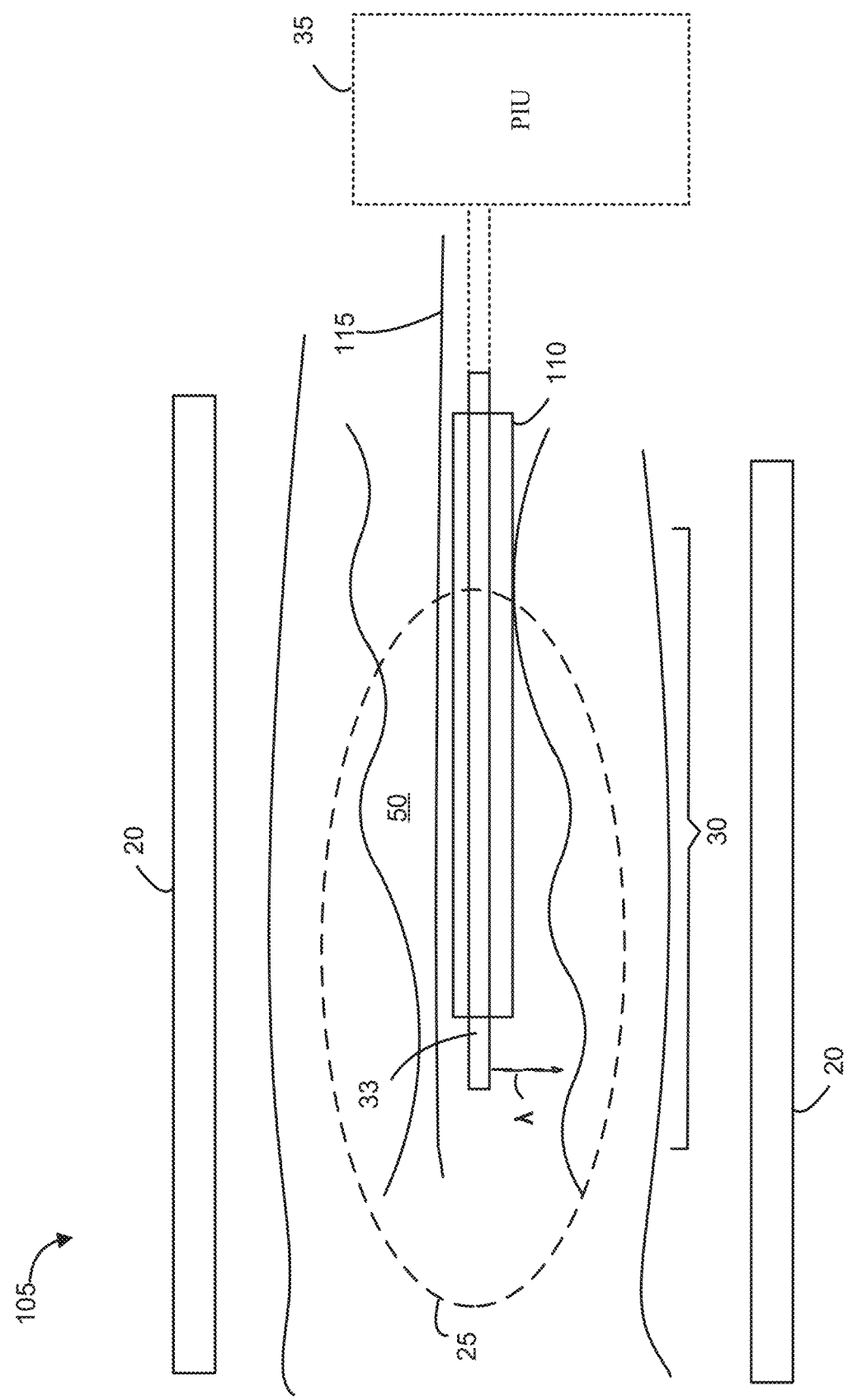
FIG. 2A shows a schematic diagram of a region of interest for a subject and features of a catheter-based data collection probe in accordance with an illustrative embodiment of the invention.

In part, embodiments of the invention relate to co-registration of intravascular images or data acquired by an imaging catheter which traverses a blood vessel, and external angiographic images of that vessel taken at the time of the catheter's traversal. A magnified, although also a generalized schematic view, of the region of interest is shown in FIG. 2A.

In a typical OCT data acquisition procedure, a catheter is inserted over a guidewire to steer the probe to the distal end of a target blood vessel. The probe 30 can include one or more markers. In one embodiment, the marker disposed on the probe 30 is a radiopaque marker band. The torque wire 110, which partially surrounds optical fiber 33, is also shown in FIG. 2A. The probe 30 is disposed in the lumen 50 of the blood vessel. A guidewire 115 is also shown in the lumen 50. The guidewire 115 is used to position the probe tip and the torque wire which are disposed in a catheter to the lumen. Light λ from the probe tip is shown being directed to the wall of the blood vessel having lumen 50.

Figure 2B:
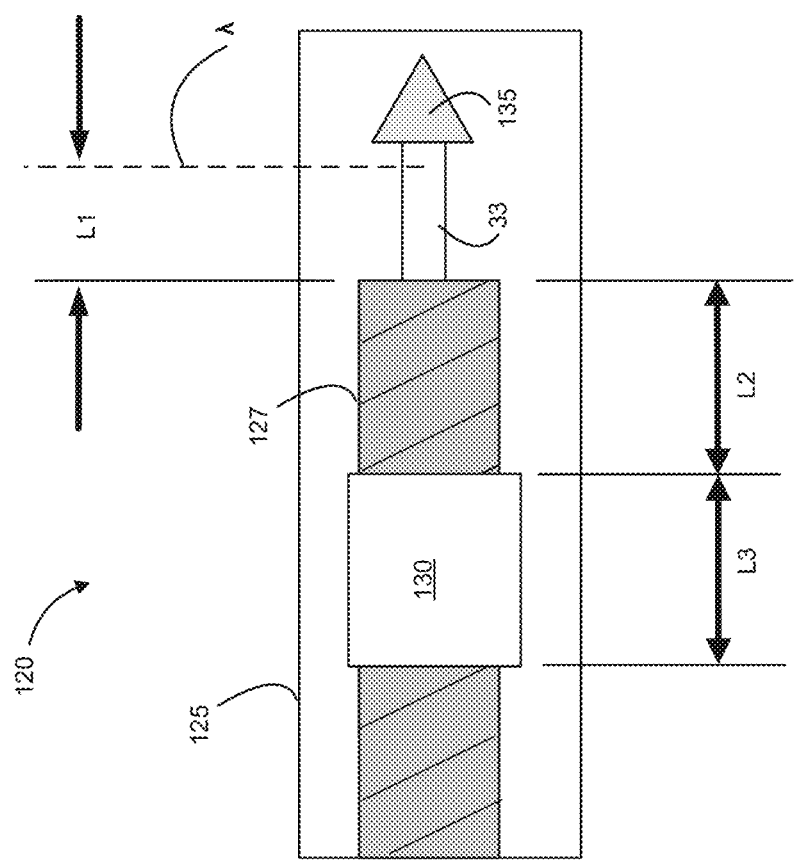
FIG. 2B shows a schematic diagram of a catheter-based data collection probe including a marker in accordance with an illustrative embodiment of the invention.

Additional details relating to an exemplary intravascular data collection probe is shown in FIG. 2B. As shown in FIG. 2B, an intravascular data collection probe 120 such as an OCT, IVUS, FRR, or other data collection probe, includes an optical fiber 33 configured to direct light as shown by the dotted line as part of a probe tip. A sheath such as a polymer sheath 125 surrounds the probe tip which includes a beam directing element such as lens or a reflector. Light is shown exiting the beam director along the dotted line. The optical fiber 33 is disposed in a torque wire 110 which is also disposed within the sheath 120. The optical fiber 33 is coupled to PIU 35 as shown.

As shown in FIG. 2B, a marker or marker band 130 such as a radiopaque marker is part of the data collection probe 120. The markers are detectable by angiography systems and can be tracked as they move across frames of angiography data. As shown, the distance from the right edge of the torque wire 127 to the beam directing element such as lens or a reflector is L1.

Additionally, the distance from the right edge of the torque wire 127 to the right edge of the marker 130 is L2. The thickness of the marker 130 is L3. The distance from the distal edge of the marker 130 (shown as left side of marker) to the torque wire 127 is L3+L2. In one embodiment, L1 ranges from about 0.3 mm to about 0.9 mm. In one embodiment, L2 ranges from about 0.6 mm to about 1.4 mm. In one embodiment, L3 ranges from about 0.5 mm to about 1.5 mm.

In one embodiment, a data collection probe such as an OCT probe can include three radiopaque marker bands. The distal marker located at the distal end of the probe remains stationary throughout the acquisition. The middle marker is located at the imaging core, which resides 27 mm from the distal marker before pullback. The proximal marker is located 50 mm from the imaging core and this distance remains fixed during the pullback.

Figure 6A:
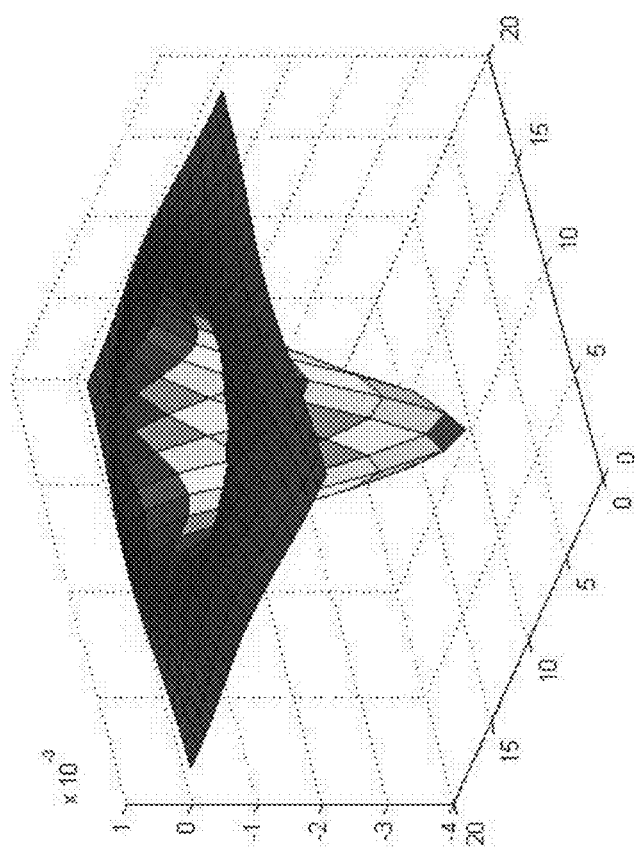
FIG. 6A is an exemplary bottom hat filter configured to enhance blobs or other pixel regions in an angiography image that are likely to be a marker from a probe in accordance with an illustrative embodiment of the invention.
Figure 6B:
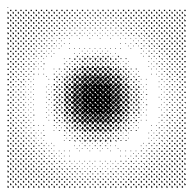
FIG. 6B is an exemplary blob corresponding to a subset of pixels from an angiography region that has been enhanced by the application of the filter from FIG. 6A in accordance with an illustrative embodiment of the invention.
Figure 6C:
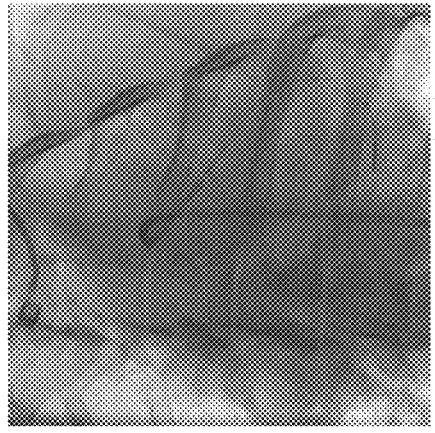
FIG. 6C is an original angiography image without contrast agent prior to wire detection in accordance with an illustrative embodiment of the invention.

During the pullback, a processor-based system, such as system 22 in FIG. 1, records live angiograms, and displays blood vessels with a contrast agent and the marker or the probe. Typically, the markers are visible most of the time. Optionally, some frames are recorded without any contrast agent, such as shown in FIG. 6C, such that the guidewire and markers are clearly visible. This provides a good indication of the pullback track through the vessel.

Figure 3A:
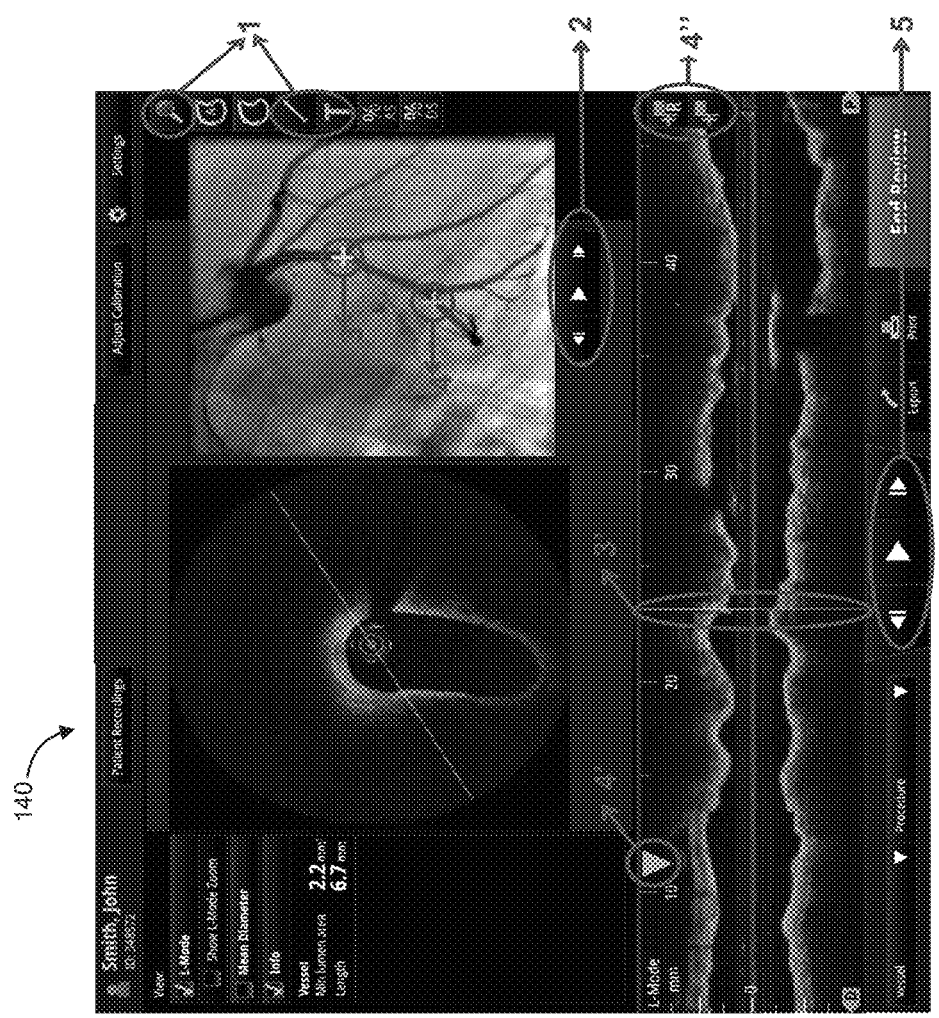
FIG. 3A shows an image of a graphic user interface suitable for controlling or reviewing data and images generated by the system of FIG. 1 and/or the methods and software modules described herein in accordance with an illustrative embodiment of the invention.

FIG. 3A shows an exemplary graphic user interface configured to display multiple panels. The graphic user interface can be implemented using a computing device such as the server 50 or workstation 87 or another suitable computing device. The upper right panel shows frame angiography image data. As shown in the image, a section of a blood vessel disposed between an upper point or cursor 3 and a lower point or cursor 4 was imaged using an intravascular imaging technology as part of a pullback. Specifically, the angiographic data was obtained while an OCT pullback was performed.

An exemplary cross-section of the artery is shown in the upper left panel. In the upper left OCT image side branch is shown to the right of the cross-section of the data collection probe. Lower panel, which substantially spans the user interface, includes the longitudinal image of the blood vessel disposed between the distal end point and the proximal end point shown in the angiography image shown by points or cursors 3, 4. The magnifying glass icon can be used to zoom in or out on either the OCT or angiography image. The pencil icon can be used to make measurements on either the OCT or angiography image. The angiography frames of data can be played as video in the upper right panel by using the play, review, or forward video user interface controls.

In the upper left OCT image, the angled axis shows the cut plane used to display the longitudinal mode in the lower panel. The longitudinal mode is generated by combining a plurality cross-sectional view such as that shown in the upper left quadrant interface. In the L mode the triangle 4' is configured to show a bookmarked location of a frame of interest. Longitudinal view or L mode can be advanced or reviewed or shown in an animated manner using the review, play, and forward L mode user interface but the vertical line shown in the L mode corresponds to the cross-sectional slice of the blood vessel shown in the cross-sectional OCT image above. By selecting the play and review buttons in the L mode the corresponding vertical line advances or retreats as different cross-sections are shown in the upper OCT image as the vertical line moves in the L mode in the lower panel.

Figure 3B:
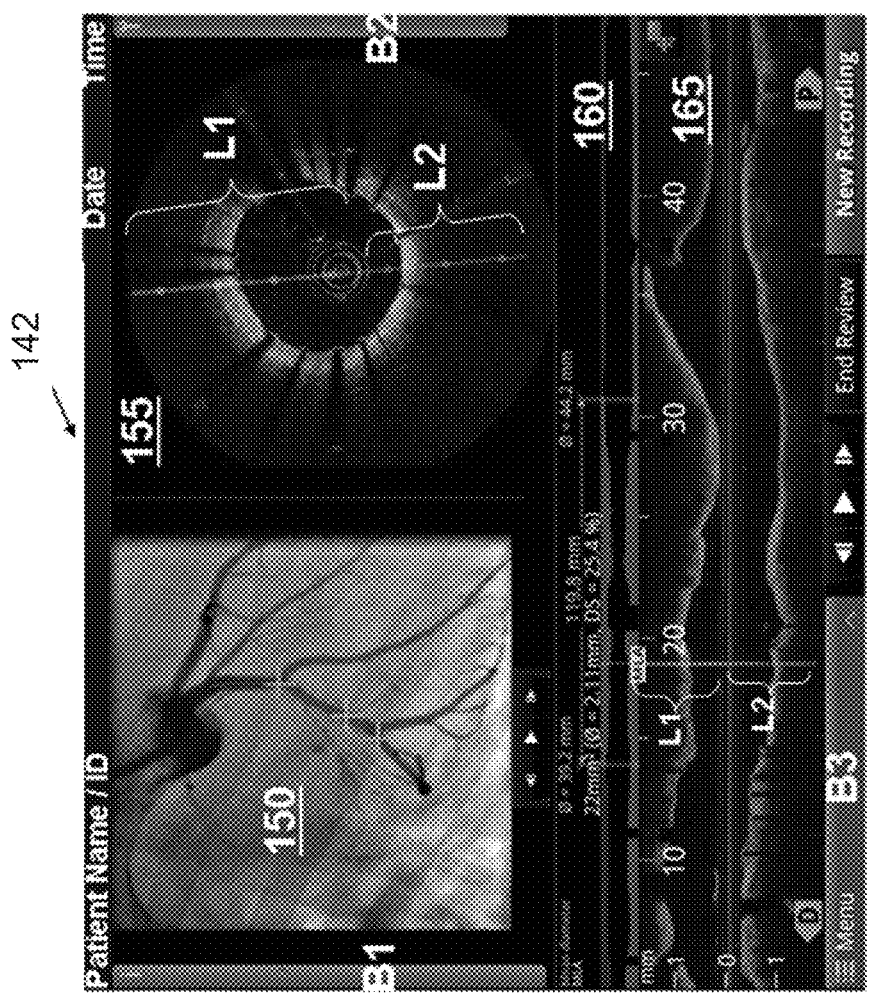
FIG. 3B shows an image of another graphic user interface suitable for controlling or reviewing data and images generated by the system of FIG. 1 and/or the methods and software modules described herein in accordance with an illustrative embodiment of the invention.

In one embodiment, the computing device used to display and execute the user interfaces of FIGS. 3A and 3B includes memory storage which includes image data such as cross-sectional views of a blood vessel. The computing device can include machine readable medium or other memory that includes one or more software modules for displaying a graphical user interface such as interface 142. The interface can include a plurality of panels, menus or other displayable regions. These panels or regions can be displayed on one or more monitors such as display 82. The computing device can exchange data such as image data with the monitor 23 using a network which can include one or more wired, optical, wireless or other data exchange connections.

A controller or input device 127 can be in wired, optical, or otherwise in communication with the other devices or systems shown over the network 120. The controller can be used to send command signals to the computing system 100 which is running the interface 142. The interface 142 can display data from the system 5 of FIG. 1, system 300 of FIG. 14, or other sources of data, systems or software modules described herein. The interface 142 can include one or more menus and other sections that change in response to control signals from controller 127. The controller 127 can include a processor or suitable programmable ASIC. The control signals can be sent over the network 120 or via another connection.

The computing device 100 may include a server computer, a client user computer, a personal computer (PC), a laptop computer, a tablet PC, a desktop computer, a control system, a microprocessor or any computing device capable of executing a set of instructions (sequential or otherwise) that specify actions to be taken by that computing device. Further, while a single computing device is illustrated, the term "computing device" shall also be taken to include any collection of computing devices that individually or jointly execute a set (or multiple sets) of instructions to perform any one or more of the software features or methods such as interface 142.

FIG. 3B shows a representation of a graphic user interface 142. The interface 142 includes a plurality of panels. As shown, there are four main panels 150, 155, 160, and 165 in one embodiment. These include an auxiliary display panel 150 which shows angiography data in this embodiment, a cross-sectional view or B mode display panel 155, a lumen profile panel 160, and an L mode display panel 165. In one embodiment, the interface also includes multiple toolbars B1, B2, and B3. In panel 150, three markers are shown as crosses superimposed over the angiography image. The top marker corresponds to a proximal reference frame shown in panel 160. The middle marker corresponds to a minimum lumen area frame shown in panel 160 or an active OCT frame shown in panel 155. The bottom marker corresponds to a distal reference frame shown in panel 160. The angiography frames and OCT frames of image data that can be displayed using interfaces in FIGS. 3A and 3B can be processed and co-registered as outlined herein. In one embodiment, the commuting device accesses a co-registration table to display the co-registered frames.

FIG. 3B shows a minimum lumen area plot as part of the lumen profile for the blood vessel imaged during a pullback of the OCT probe in panel 160. The D and P arrows show proximal and distal directions along the imaged blood vessel. The cut plane shown as a line having sections L1 and L2 is shown in the cross-sectional view of panel 155 and also shown by sections L1 and L2 in the L-mode panel 165. An information bar B1, a measurement bar B2, and a menu bar B3 are shown.

As shown, the distance of a blood vessel such as an artery can be measured relative to two endpoints as shown by the exemplary measurement distances of 119.88 mm. In addition, the mean diameter can be shown at each end of the selected reference frames for measuring the vessel such as by the mean diameter values of 39.2 mm and 44.2 mm at the distal and proximal reference frames respectively. As shown, the MLA is about 22 mm². At the MLA frame, the vessel mean diameter is about 2.11 mm and the percent diameter stenosis is 25.4% relative to the average diameters of the proximal and distal reference frames.

All three images shown in the user interface of FIGS. 3A and 3B are co-registered such that movement along the line between the ends of the blood vessel in the angiographic image can be shown by a moving point that synchronizes with the frames in the OCT images. Accordingly as one moves along the blood vessel segment, movement along the centerline shown in the angiographic image is also shown by a moving frame identifier in the cross-sectional OCT image or the L mode OCT image or both.

Initially, the proximal marker band may reside near the ostium of the coronary branch, thus it is occluded by a cloud of contrast agent during the pullback. The catheter is pulled back at constant speed through the vessel. Due to different foreshortening of blood vessel segments along the pullback, the marker does not move at constant speed in the angiography image plane (2D). Furthermore, due to the cardiac motion, the marker exhibits a distinctive "sawing" motion relative to the anatomy of the vessel. In some of the angiography frames, the marker bands appear blurred/faint due to fast pullback motion combined with fast cardiac motion. The contrast of the marker in the local neighborhood might be low. Other features, such as foreshortened bifurcations, background structures and the like, may be mistaken for any of the marker bands.

The data collection system 5 includes a noninvasive imaging system such as a nuclear magnetic resonance, x-ray, computer aided tomography, or other suitable noninvasive imaging technology. As shown as a non-limiting example of such a noninvasive imaging system, an angiography system 20 such as suitable for generating cines is shown. The angiography system 20 can include a fluoroscopy system. Angiography system 20 is configured to noninvasively image the subject 10 such that frames of angiography data, typically in the form of frames of image data, are generated while a pullback procedure is performed using a probe 30 such that a blood vessel in region 25 of subject 10 is imaged using angiography in one or more imaging technologies such as OCT or IVUS, for example.

The angiography system 20 is in communication with an angiography data storage and image management system 22, which can be implemented as a workstation or server in one embodiment. In one embodiment, the data processing relating to the collected angiography signal is performed directly on the detector of the angiography system 20. The images from system 20 are stored and managed by the angiography data storage and image management 22. In one embodiment system server 50 or workstation 87 handle the functions of system 22. In one embodiment, the entire system 20 generates electromagnetic radiation, such as x-rays. The system 20 also receives such radiation after passing through the subject 10. In turn, the data processing system 22 uses the signals from the angiography system 20 to image one or more regions of the subject 10 including region 25.

As shown in this particular example, the region of interest 25 is a subset of the vascular or peripherally vascular system such as a particular blood vessel. This can be imaged using OCT. A catheter-based data collection probe 30 is introduced into the subject 10 and is disposed in the lumen of the particular blood vessel, such as for example, a coronary artery. The probe 30 can be a variety of types of data collection probes such as for example an OCT probe, an FFR probe, an IVUS probe, a probe combining features of two or more of the foregoing, and other probes suitable for imaging within a blood vessel. The probe 30 typically includes a probe tip, one or more radiopaque markers, an optical fiber, and a torque wire. Additionally, the probe tip includes one or more data collecting subsystems such as an optical beam director, an acoustic beam director, a pressure detector sensor, other transducers or detectors, and combinations of the foregoing.

For a probe that includes an optical beam director, the optical fiber 33 is in optical communication with the probe with the beam director. The torque wire defines a bore in which an optical fiber is disposed. In FIG. 1, the optical fiber 33 is shown without a torque wire surrounding it. In addition, the probe 30 also includes the sheath such as a polymer sheath (not shown) which forms part of a catheter. The optical fiber 33, which in the context of an OCT system is a portion of the sample arm of an interferometer, is optically coupled to a patient interface unit (PIU) 35 as shown.

The patient interface unit 35 includes a probe connector suitable to receive an end of the probe 30 and be optically coupled thereto. Typically, the data collection probes 30 are disposable. The PIU 35 includes suitable joints and elements based on the type of data collection probe being used. For example a combination OCT and IVUS data collection probe requires an OCT and IVUS PIU. The PIU 35 typically also includes a motor suitable for pulling back the torque wire, sheath, and optical fiber 33 disposed therein as part of the pullback procedure. In addition to being pulled back, the probe tip is also typically rotated by the PIU 35. In this way, a blood vessel of the subject 10 can be imaged longitudinally or via cross-sections. The probe 30 can also be used to measure a particular parameter such as an FFR or other pressure measurement.

In turn, the PIU 35 is connected to one or more intravascular data collection systems 40. The intravascular data collection system 40 can be an OCT system, an IVUS system, another imaging system, and combinations of the foregoing. For example, the system 40 in the context of probe 30 being an OCT probe can include the sample arm of an interferometer, the reference arm of an interferometer, photodiodes, a control system, and patient interface unit. Similarly, as another example, in the context of an IVUS system, the intravascular data collection system 40 can include ultrasound signal generating and processing circuitry, noise filters, rotatable joint, motors, and interface units. In one embodiment, the data collection system 40 and the angiography system 20 have a shared clock or other timing signals configured to synchronize angiography video frame time stamps and OCT image frame time stamps.

In addition to the invasive and noninvasive image data collection systems and devices of FIG. 1, various other types of data can be collected with regard to region 25 of the subject and other parameters of interest of the subject. For example, the data collection probe 30 can include one or more pressure sensors such as for example a pressure wire. A pressure wire can be used without the additions of OCT or ultrasound components. Pressure readings can be obtained along the segments of a blood vessel in region 25 of the subject 10.

Such readings can be relayed either by a wired connection or via a wireless connection. As shown in a fractional flow reserve data collection system 45, a wireless transceiver 47 is configured to receive pressure readings from the probe 30 and transmit them to a system to generate FFR measurements or more locations along the measured blood vessel. One or more displays 82 can also be used to show an angiography frame of data, an OCT frame, user interfaces for OCT and angiography data and other controls and features of interest.

The intravascular image data such as the frames of intravascular data generated using the data collection probe 30 can be routed to the data collection processing system 40 coupled to the probe via PIU 35. The noninvasive image data generated using angiography system 22 can be transmitted to, stored in, and processed by one or more servers or workstations such as the co-registration server 50 workstation 87. A video frame grabber device 55 such as a computer board configured to capture the angiography image data from system 22 can be used in various embodiments.

In one embodiment, the server 50 includes one or more co-registration software modules 60 that are stored in memory 70 and are executed by processor 80. The server 50 can include other typical components for a processor-based computing server. Or more databases such as database 90 can be configured to receive image data generated, parameters of the subject, and other information generated, received by or transferred to the database 90 by one or more of the systems devices or components shown in FIG. 1. Although database 90 is shown connected to server 50 while being stored in memory at workstation 87, this is but one exemplary configuration. For example, the software modules 60 can be running on a processor at workstation 87 and the database 90 can be located in the memory of server 50. The device or system use to run various software modules are provided as examples. In various combinations the hardware and software described herein can be used to obtain frames of image data, process such image data, and register such image data.

As otherwise noted herein, the software modules 60 can include software such as preprocessing software, transforms, matrices, and other software-based components that are used to process image data or respond to patient triggers to facilitate co-registration of different types of image data by other software-based components 60 or to otherwise perform such co-registration.

The database 90 can be configured to receive and store angiography image data 92 such as image data generated by angiography system 20 and obtained by the frame grabber 55 server 50. The database 90 can be configured to receive and store OCT image data 95 such as image data generated by OCT system 40 and obtained by the frame grabber 55 server 50. The database 90 can be configured to receive and store an angiography table such as that shown in FIG. 14 and a co-registration table such as that shown in FIG. 15.

In addition, the subject 10 can be electrically coupled via one or more electrodes to one more monitors such as, for example, monitor 49. Monitor 49 can include without limitation an electrocardiogram monitor configured to generate data relating to cardiac function and showing various states of the subject such as systole and diastole. Knowing the cardiac phase can be used to assist the tracking of vessel centerlines, as the geometry of the heart, including the coronary arteries, is approximately the same at a certain cardiac phase, even over different cardiac cycles.

Hence, if the angiography data spans a few cardiac cycles, a first-order matching of vessel centerline at the same cardiac phase may assist in tracking the centerlines throughout the pullback. In addition, as most of the motion of the heart occurs during the systole, vessel motion is expected to be higher around the systole, and damp towards the diastole. This provides data to one or more software modules as an indication of the amount of motion expected between consecutive angiography frames. Knowledge of the expected motion can be used by one or more software modules to improve the tracking quality and vessel centerline quality by allowing adaptive constraints based on the expected motion.

The use of arrow heads showing directionality in a given figure or the lack thereof are not intended to limit or require a direction in which information can flow. For a given connector, such as the arrows and lines shown connecting the elements shown in FIG. 1, for example, information can flow in one or more directions or in only one direction as suitable for a given embodiment. The connections can include various suitable data transmitting connections such as optical, wire, power, wireless, or electrical connections.

Furthermore, although the FFR data collection system 45 is shown as having a wireless system 47 suitable for sending and receiving information wirelessly, the other systems and components shown in FIG. 1 also include wireless systems such as system 47 and can send and receive information wirelessly in one embodiment.

One or more software modules can be used to process frames of angiography data received from an angiography system such as system 22 shown in FIG. 1. Various software modules which can include without limitation software, a component thereof, or one or more steps of a software-based or processor executed method can be used in a given embodiment of the invention.

Examples of such software modules can include without limitation a video processing software module, a preprocessing software module, an image file size reduction software module, a catheter removal software module, a shadow removal software module, a vessel enhancement software module, a blob enhancement software module, a Laplacian of Gaussian filter or transform software module, a guidewire detection software module, an anatomic feature detection software module, stationary marker detection software module, a background subtraction module, a Frangi vesselness software module, an image intensity sampling module, a moving marker software detection module, iterative centerline testing software module, a background subtraction software module, a morphological close operation software module, a feature tracking software module, a catheter detection software module, a bottom hat filter software module, a path detection software module, a Dijkstra software module, a Viterbi software module, fast marching method based software modules, a vessel centerline generation software module, a vessel centerline tracking module software module, a Hessian software module, an intensity sampling software module, a superposition of image intensity software module and other suitable software modules as described herein. The software module 60 shown in FIG. 1 can include one or more of the foregoing software modules and other software modules described herein.

Image Data Processing Features and Exemplary Embodiments

Figure 4A:
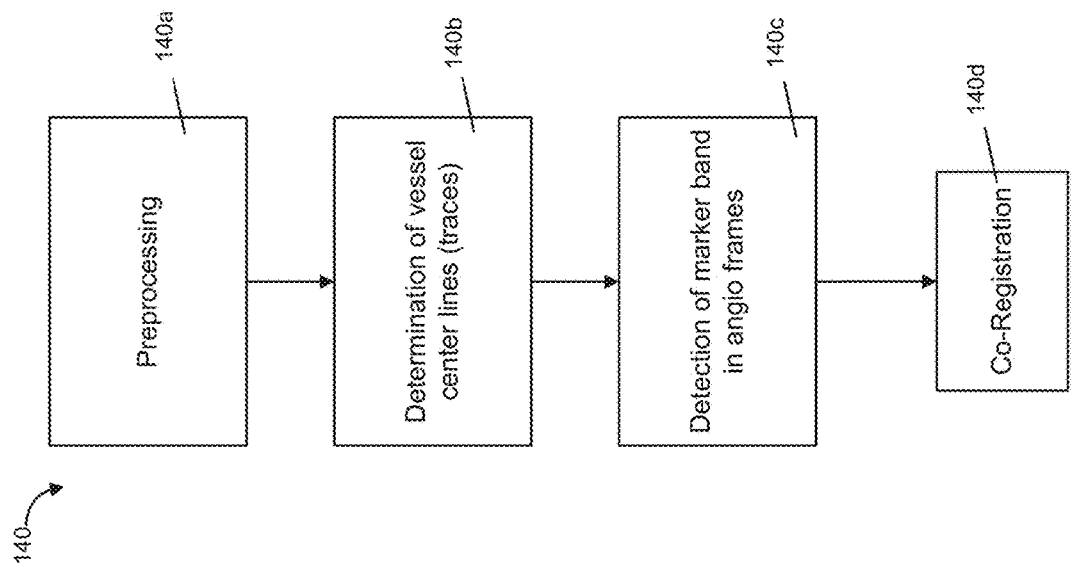
FIGS. 4A and 4B are schematic diagrams showing processing stages or processing steps suitable for processing and using image data in accordance with an illustrative embodiment of the invention.
Figure 4B:
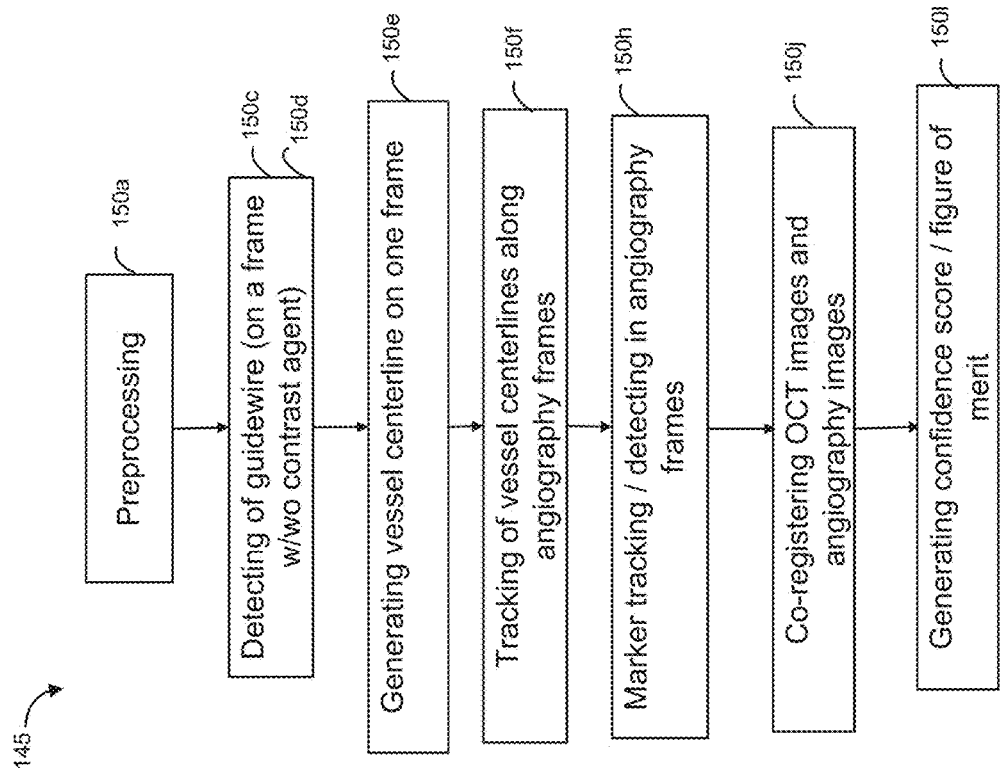

As shown in FIGS. 4A and 4B, various processing stages, steps or software modules are generalized to provide a high level summary of the process of co-registering angiography image data and image data obtained using an intravascular imaging technology such as OCT, IVUS, or others. In one embodiment, frames of angiography data are captured on an OCT or IVUS server or workstation using a frame grabber or other data capture device. Capturing images from both imaging modalities in real time ensures accurate time stamping of the two sources with respect to one another. DICOM angiography data acquisition time cannot be inherently calibrated to match the timing of the OCT data. For example, a video software module can be controlled via a user interface to present angiography video to a frame grabber which can in turn obtain and store individual frames of angiography data with a time stamp. In one embodiment, the OCT data and the angiography data are date stamped by two respective processes that run in parallel on the same computer and hence share the same time base.

Once the angiography data frames have been cached or otherwise stored, each of the stored frames can be modified during a preprocessing stage. Various matrices such as convolution matrices, Hessians, and others can be applied on a per pixel basis to change the intensity, remove, or otherwise modify a given angiography image frame. As discussed herein, the preprocessing stage effectively enhances or modifies or removes features of the angiography images to increase the accuracy, processing speed, success rate, and other properties of subsequent processing stages.

As shown in FIG. 4A, various software-based processing stages 140 are shown. Initially, one or more frames of angiography images are processed during a preprocessing stage 140*a* prior to various detection and tracking stages in support of co-registering such frames with other image data obtained with another imaging technology such as OCT, IVUS, others, and combinations thereof. The next stage is a vessel centerline determination or calculation stage 140*b*. As shown in the user interface of FIG. 3, a vessel centerline is generated by one or more software modules and superimposed or otherwise displayed relative to the angiography image.

In one embodiment, the centerline represents a trajectory of the probe such as the data collection probe 30 of FIG. 1 through the blood vessel being imaged during the pullback. In one embodiment, the centerline is also referred to as a trace. Another stage is the detection of marker band in angiography frames 140*c*. In one embodiment, the last stage is a co-registration stage. These stages and the other stages and methods described herein can be performed in different orders, interactively, in parallel or in series or combinations thereof. Additional steps and stages can also be added before or after or in between a given stage or step. Additional examples of exemplary stages and steps reciting further details are shown in FIGS. 4B and 5A-5C.

Figure 6D:
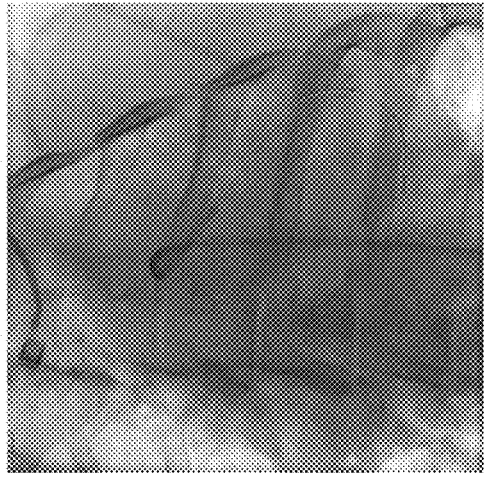
FIG. 6D is an exemplary angiography image showing the results of guidewire detection on a frame without contrast agent in accordance with an illustrative embodiment of the invention.
Figure 6E:
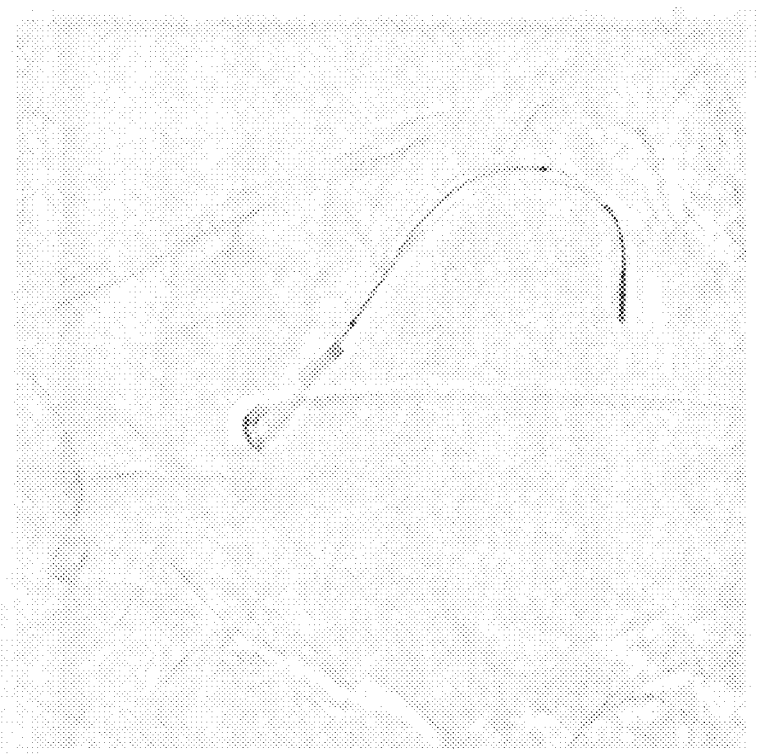
FIG. 6E is an exemplary angiography image showing the results of guidewire enhancement after the application of a bottom hat operator in accordance with an illustrative embodiment of the invention.
Figure 6F:
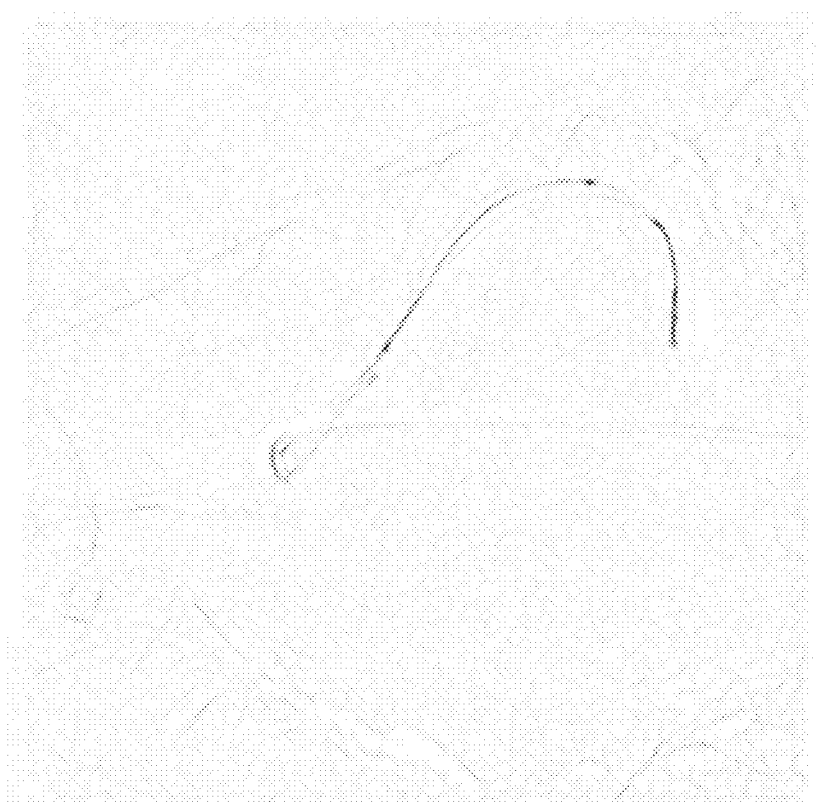
FIG. 6F is an exemplary angiography image showing the results of guidewire enhancement after the application of a Hessian operator having a scale value of one in accordance with an illustrative embodiment of the invention.
Figure 6G:
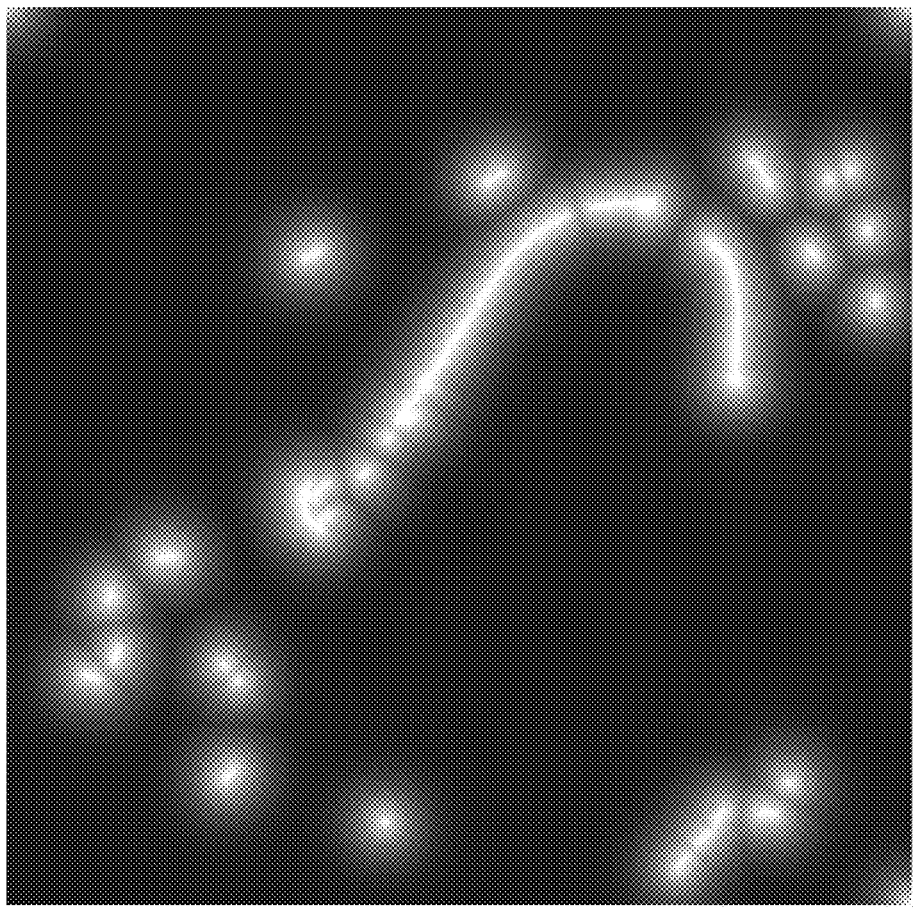
FIG. 6G is an exemplary potential generated based on the guidewire suitable for use with a fast marching method (FMM) process in accordance with an illustrative embodiment of the invention.
Figure 6H:
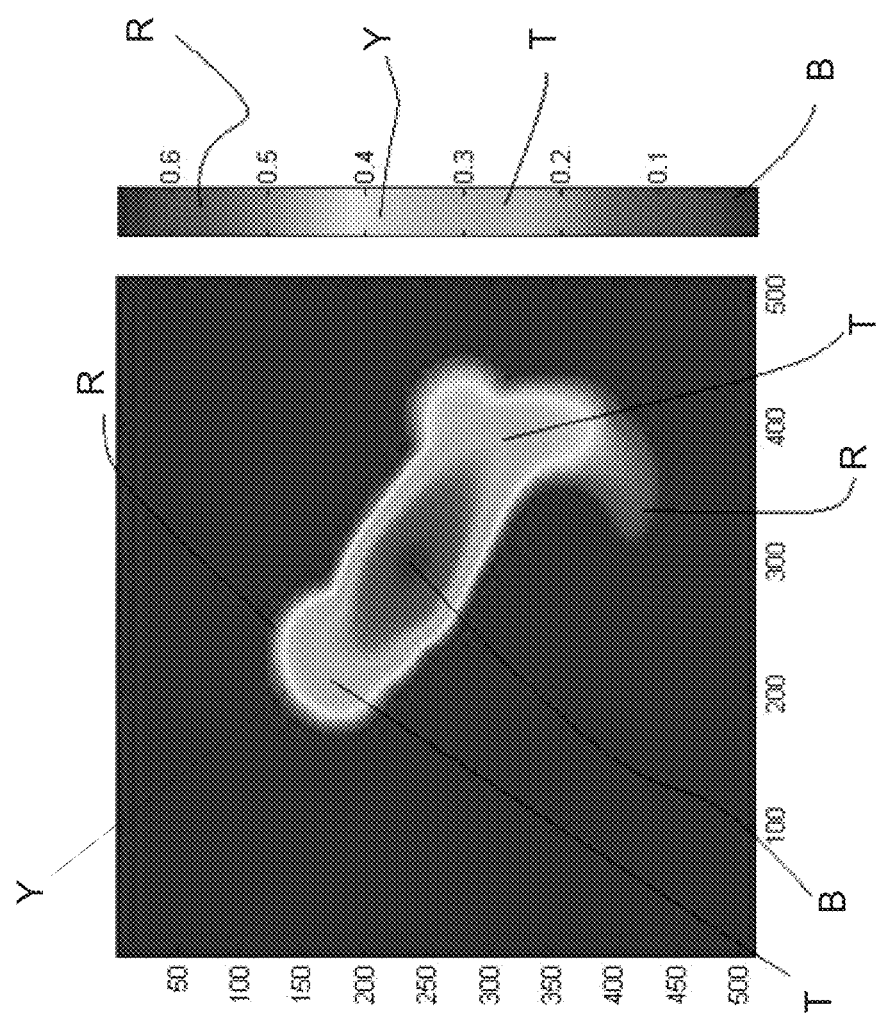
FIG. 6H is a distance map generated using an FMM process in accordance with an illustrative embodiment of the invention.
Figure 6I:
FIG. 6I is an original angiography image with contrast agent prior to catheter and shadow removal in accordance with an illustrative embodiment of the invention.
Figure 6J:
FIG. 6J is an exemplary angiography image showing the results of catheter and shadow removal in accordance with an illustrative embodiment of the invention.
Figure 6K:
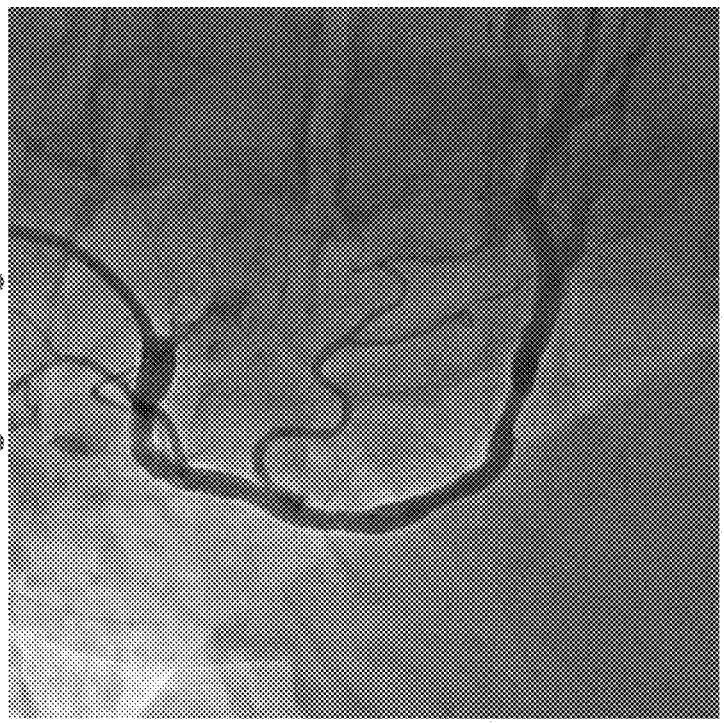
FIG. 6K is an original angiography image with contrast agent prior to shadow removal in accordance with an illustrative embodiment of the invention.
Figure 6L:
FIG. 6L is an exemplary angiography image showing the results of catheter and shadow removal in accordance with an illustrative embodiment of the invention.
Figure 6N:
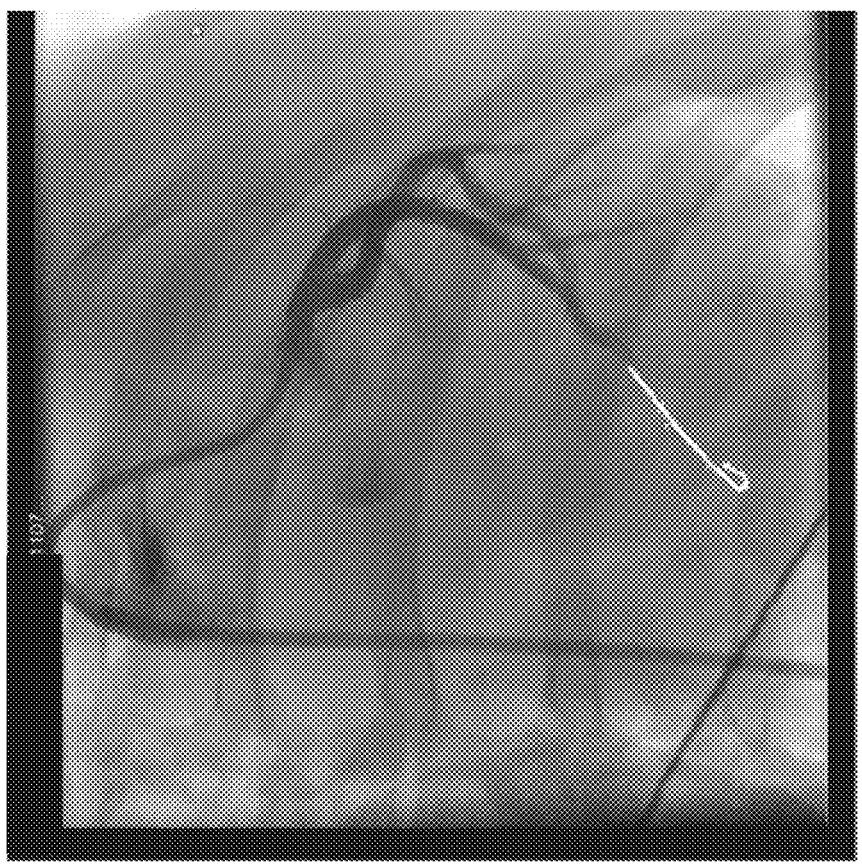
FIG. 6N is an exemplary angiography image showing the results of guidewire detection with respect to the original image of FIG. 6V in accordance with an illustrative embodiment of the invention.
Figure 6M:
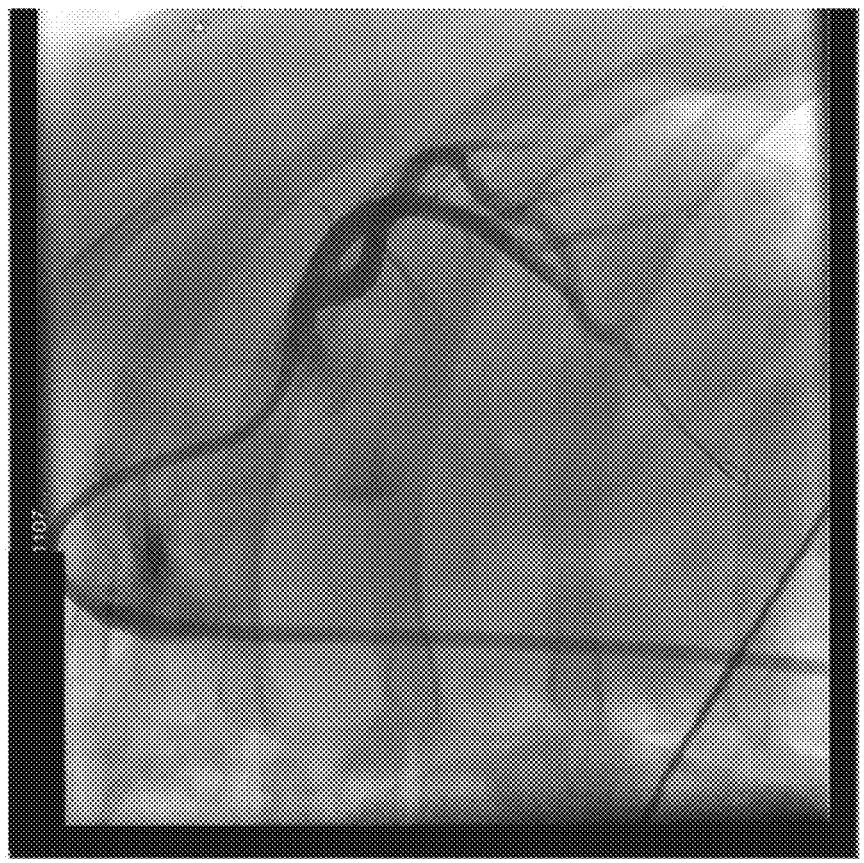
FIG. 6M is an original angiography image with contrast agent prior to guide wire detection in accordance with an illustrative embodiment of the invention.

As shown in FIG. 4B, various software-based processing stages or processing steps 145 are shown that include further detail relative to those shown in FIG. 4A. Initially, preprocessing of angiography frames is performed 150*a*. Detecting of guidewire on a frame without contrast agent is performed 150*c* as shown in FIG. 6D. FIG. 6N is an exemplary angiography image showing the results of guidewire detection. As shown in FIG. 6N, the distal part of the guidewire is detected.

Next, in one embodiment, generating vessel centerline on one frame is performed 150*e*. In one embodiment, a user input such as the selection of a guidewire endpoint in the lumen being imaged via a user interface is stored as a user selected end point alternatively referred to as a hint point. Such a hint point can be used to generate the vessel centerline on one frame such that a trace between the hint point and a distal point is generated for the relevant frames of angiography data. In one embodiment, such a relevant frame is obtained without contrast solution being disposed in the blood vessel.

Still referring to FIG. 4B, tracking of vessel centerlines along angiography frames is performed 150*f*. In one embodiment, such tracking of vessel centerlines is performed with regard to all or substantially all of the angiography frames obtained during the pullback. Radio-opaque marker tracking and/or marker detecting in angiography frames is performed 150*h*. In one embodiment, a Viterbi algorithm is used to perform marker tracking. Co-registering OCT images and angiography images is performed 150*j*. Generating a confidence score/figure of merit is performed 150*l*.

Generating a confidence score/figure of merit (FOM) is performed using one or more software modules 150*l*. In one embodiment, the confidence score or (FOM) is provided to a user by graphical representation on a computer monitor, for example by providing a color-code on the X-ray or OCT image indicating regions of the OCT pullback that have high or low confidence of being co-registered. Regions of low confidence may, for example, be indicated by a red strip or bar on the X-ray image near the vessel segment where low FOM values were obtained. The FOM/Score reflects a confidence measure in the returned results. The score is in the range of [0, 1] where 0 reflects the lowest confidence and 1 reflects the highest. A FOM threshold value can be selected to define a boundary between high confidence and low confidence co-registration results. The threshold value can be chosen to give a desired sensitivity and specificity for identifying high-error locations by producing a receiver-operator curve (ROC). If low FOM values are obtained for a large portion of the frames in a given pullback, such that the overall quality of the co-registration is questionable, no co-registration results may be displayed to the user.

The FOM determination is a scoring process that is based upon one or more factors such as the quality of the detected blob (contrast or intensity of detected blob compared to that of immediate neighborhood, shape, size, etc.), the distance of the detected blob from its nominally expected position (based on pullback speed, frame rate calculations), the number of blob candidates that were found in the same vicinity (the more candidates, the lower the FOM), and intensity-based z-score, the overall score of the Viterbi algorithm (how well the overall collection of detected blobs represents a pullback) and other factors and measures. In one embodiment, a weighted average including one or more of the parameters recited herein can be used to generate a FOM or score.

Figure 5A:
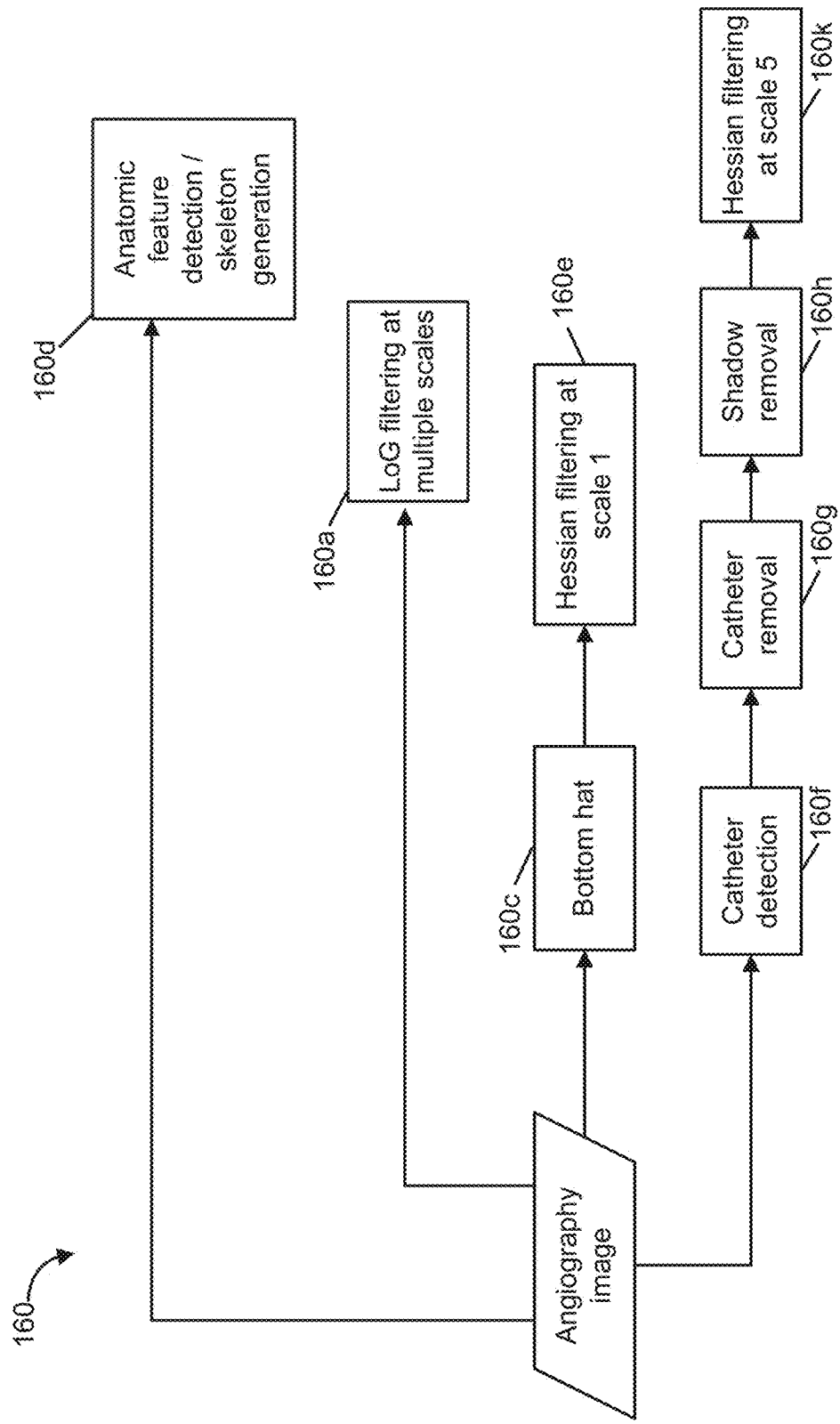
FIG. 5A shows a flow chart relating to some exemplary preprocessing steps or stages in accordance with an illustrative embodiment of the invention.

The various steps and stages shown in FIG. 4A and FIG. 4B and as otherwise described herein can be performed automatically in whole or in part in various embodiments. Additional details relating to some specific examples of some of the steps and methods of FIG. 4A and FIG. 4B are described herein, such as with respect to FIGS. 5A-5C. For example, FIG. 5A shows a flow chart relating to some exemplary preprocessing steps or stages.

Exemplary Angiography Image Data Preprocessing Embodiments

In part, as shown in FIGS. 4A and 4B and otherwise described herein, in part, the invention includes one or more preprocessing stages, preprocessing software modules, and related methods with regard to the collected frames of angiography data. In one embodiment, image preprocessing is performed on a per frame basis with respect to the frames of angiography image data such as the data generated by system 20 of FIG. 1. The preprocessing stage can include, without limitation, methods, stages, and software components, and other components suitable to perform vessel enhancement, catheter removal, shadow removal, heart shadow removal, blob enhancement such as by applying a multiscale Laplacian of Gaussian, detection of anatomic features, skeleton generation, angiography image size reduction, background subtraction, bottom hat filters, and others.

Various matrices such as Hessians and other types of filters and masks can be applied to enhance the frames of angiography data prior to them being subjected to further processing to track markers, generate centerlines, be co-registered with OCT, IVUS, or other images or data. One or more image processing stages can be used to preprocess frames of angiography data received from an angiography system such as system 22 or the server or workstation 50 and 87 shown in FIG. 1.

FIG. 5A shows a process flow 160 relating to some additional specific exemplary preprocessing steps or stages. As shown, angiography images can be processed at various stages in parallel. In one embodiment, LoG filtering is performed at multiple scales 160a. Each scale corresponds to size of an element in the image that will be acted upon by the filter. A LoG multiscale based filter can be used, in one embodiment, to enhance blobs corresponding to the moving marker on the imaging probe. Different scales are used because of the different sizes of the markers. In one embodiment, to be sensitive to different sizes of the blobs, and less sensitive to noise, the LoG operator is computed at several scales. An example of a LoG filter is shown in FIG. 6A. An example of a blob as (a set of pixels from an angiography image) corresponding to a marker that has been enhanced from applying the LoG of FIG. 6A as part of an imaging processing software enhancement is shown in FIG. 6B. In one embodiment, background subtraction to reduce the effect of static features based on an average of several frames of angiography images is performed.

In addition, in one embodiment, a bottom hat filter or transform 160c can be applied to the angiography data to increase the visibility of the guidewire in the image. In one embodiment, the bottom hat filter is configured to erase features larger than the size of particular structural element in a given angiography figure such as the diaphragm, skeletal features, etc. An example of a bottom hat filter or bottom hat operator applied to an angiography image is shown in FIG. 6E. In one embodiment, multiple image averaging is used for background subtraction. In addition, in one embodiment Hessian filtering at a scale, such as scale 1, is performed 160e following the bottom hat filter or transform. Such a Hessian filter at scale 1 is performed in order to enhance the wire, while smoothing the noisy image after the application of the bottom hat operator. An example of a Hessian filter at scale 1 applied to an image is shown in FIG. 6F.

In one embodiment, a morphologic close operation is performed on the image data. The morphologic close operation is mainly used to fill in possible gaps, sometimes obtained in the step of applying the bottom hat transform. The bottom hat transform is applied with a small filter kernel in order to enhance narrow features such as a guidewire.

Binary Image Map Features

For each angiography image, a set of preprocessing steps is applied to create a binary map which is used for determining where contrast agent is present. In one embodiment, a binary map refers to an image the same size as the original angiography image, where a pixel is either black or white—black for a pixel with dye, white for pixel without dye or vice versa. The binary map may have areas of vessel pixels separated due to the inherent imperfection of the binary map. A distance map can then be computed based on the binary map. An exemplary distance map is shown in FIG. 6H, which was computed using an FMM algorithm.

A distance map is an image the same size, where the value of each pixel is determined according to its distance from the closest "black" pixel in the binary map. Clearly, the pixels where dye was determined to be present in the binary map (the "black" pixels—for which the distance from a dye area is 0) will remain black, the pixels immediately surrounding an area of black pixels (for whom the distance from a dye area is 1) will have intensity lower by "1". The next layer of pixels' intensity will be lower by "2", etc. As shown in FIG. 6H, various intensity values are mapped to pixels arranged along x and y axis for the pixel locations. A scale coded by color or other indicia can be used to map intensity values to each pixel location. In one embodiment, the scale is a color scale. Various exemplary intensity values on the scale are shown in the figure. The central region has the lowest intensity values corresponding to B. The T intensity values increase relative to the B values. The Y intensity values increase relative to the T values and the R values increase relative to the Y intensity values.

The resulting distance map is such that the areas of dye/contrast agent in the original binary map will look like ridges, with slopes going down to their sides. If two such ridges are close enough (small distance in the binary map) they will appear as connected ridges in the distance map. The dark central spot with the smallest value in the distance map belongs to the user hint point from where the front starts to propagate. Due to the configuration of the potential, it propagates along the wire. The distal end point of the trace has the highest value on the distance map. One application of a distance map is to decide which separate segments of dye/contrast agent can be connected since they are close enough. In one embodiment, a distance map is a tool that is used to determine the vessel skeleton from the binary map. The distance map can be used for various purposes.

Exemplary Anatomic Feature Detection/A Priori Data Generation Embodiments

Further, in one embodiment, as part of the preprocessing of the angiography images, anatomic feature detection is performed. In one embodiment, this can be performed to generate certain a priori information relating to the path the imaging probe takes through the blood vessel. The generation of line segments such as through a skeleton generation process can be used for feature detection. In one embodiment, a skeleton is a static object such as one or more line segments created to help trace the blood vessels of a subject being imaged.

The use of a skeleton or line segment based approach to generate a candidate path through the blood vessel for the data collection probe which can be used to inform centerline generation and marker tracking offers several advantages to forgoing the use of such an approach. For example, the skeleton based approach can prevent or eliminate certain centerline traces being generated that would otherwise pass through a side branch or the imaging probe catheter. Generating skeletons provides a method to determine an initial candidate for the geometry of the blood vessel being imaged and side branches and other blood vessels as a map or framework to facilitate centerline generation. By generating skeletons, it is possible to extract points of interest such as bifurcation points and vessel segments, to stabilize tracking of markers and centerline traces and to verify tracking quality across frames of angiography image data.

In one embodiment, the process of generating skeletons to detect anatomic features like side branches and vessel geometry is implemented during preprocessing of the angiography images 160d. Skeletons can be used for detecting anatomical features such as main bifurcation (170l) and extrapolation point (170m). In addition, skeletons can be used for detecting and generating a smooth vessel centerline (170f). For example, skeletons can be used with the Dijkstra algorithm. The skeletons can be generated based on preprocessed Hessian images. A user selected point on an angiography image, such as the image of FIG. 7A, relating to a guidewire position can be used to reduce noise and facilitate skeleton generation.

Figure 7C:
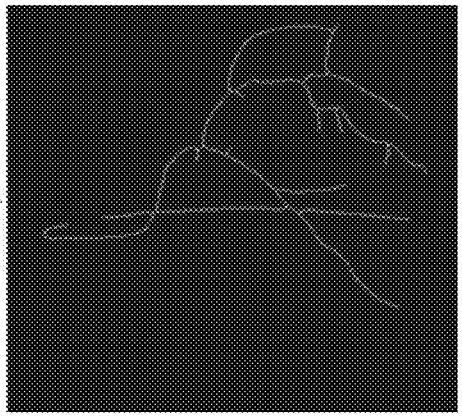
FIGS. 7A-7F show the application of different software-based image processing steps to generate a graph based upon a frame of angiography image data in accordance with an illustrative embodiment of the invention.
Figure 7B:
Figure 7A:
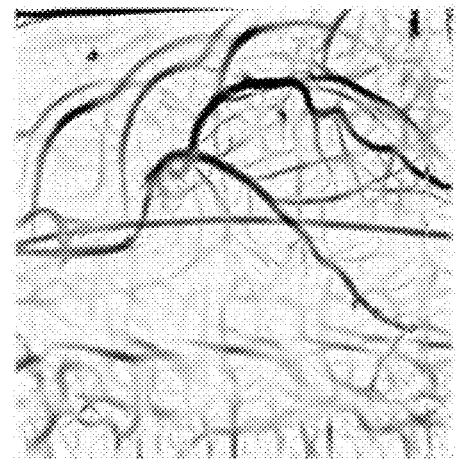
Figure 7F:
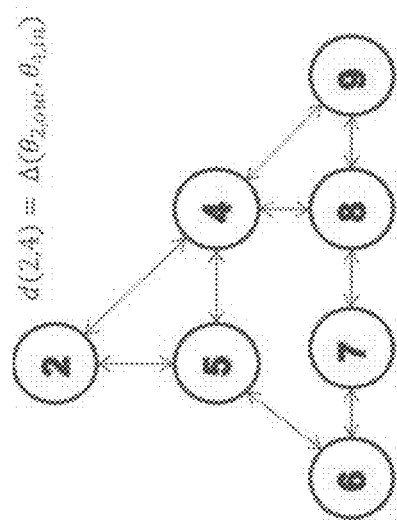
Figure 7E:
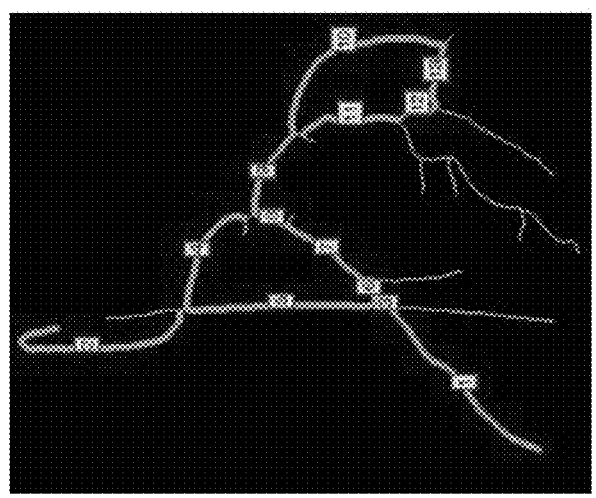
Figure 7D:
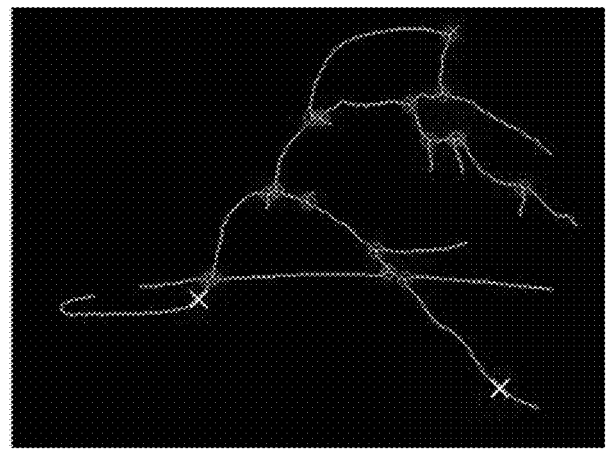

In FIG. 7D, a user selected end point and a computer determined end point are shown by the X's. A binary image generated from the Hessian image can be used to generate skeletons in the angiography image as shown in FIG. 7B. Once generated, the skeletons can be eroded to eliminate small bifurcations. For example, small branches of the skeleton can be removed or subtracted from the image until only a main trunk section remains. Thresholds relating to branch thickness and other parameters can be used to direct skeleton erosion. The removal of small branches of the skeleton can be performed on a per pixel basis in one embodiment until final skeleton results as shown in FIG. 7C.

In one embodiment, junctions are located on the skeleton by detecting bifurcations and other gaps as shown by the circled regions in FIG. 7D. These junctions are used to decompose the skeleton into branches as shown by branches 1-13 in FIG. 7E. In turn, each branch of the tree that is too small to represent a vessel branch is eroded and can be eliminated. In one embodiment, all branches are eroded equally (by the same number of pixels in length). As a result, the longer ones survive while the small ones are eliminated. The remaining skeleton branches can then be transformed into to a connected graph as shown in FIG. 7F. The distance between graph nodes, i.e., the skeleton branches, such as nodes 2 and 4 in FIG. 7F, is based on angle changes. For i=2 and j=4 for the nodes the following distance relationship can be used:

$$d(i,f)=\Delta(\theta_{i,out},\theta_{j,in})$$

to obtain d(2,4) as shown in FIG. 7F. In one embodiment, a graph searching method such as the Dijkstra shortest path algorithm or modified versions thereof is applied to the graph to obtain best candidate paths for the blood vessel in the skeleton. This is actually a modified version of the Dijkstra algorithm. The chosen path is the path between nodes in which the maximal angle change was the smallest regarding the other optional paths such as provided for by:

$$\text{path}=\min\{\max\{d\theta_j | f \in \text{path junction}\}\}$$

Figure 8C:
FIGS. 8A-8C show various best paths found through the graph generated in FIG. 7F based on a graph searching algorithm in accordance with an illustrative embodiment of the invention.
Figure 8B:
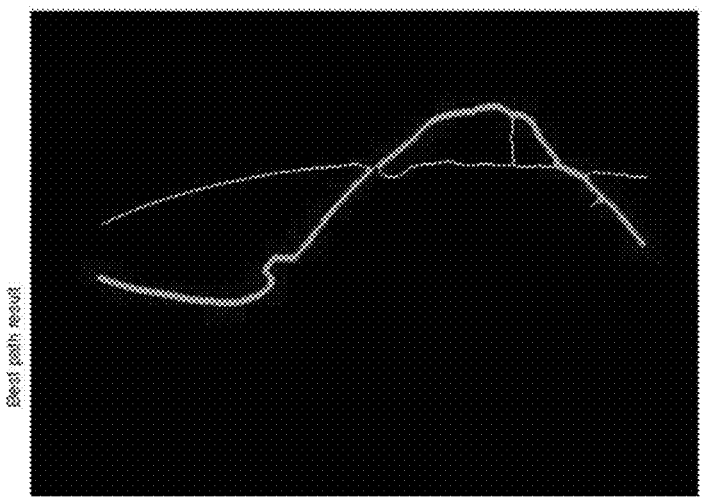
Figure 8A:

FIGS. 8A-8C show the resulting best paths found relative to the skeleton of FIG. 7E based on the application of the Dijkstra shortest path algorithm to the graph generated in FIG. 7F. FIG. 8A shows a path through nodes 2, 4, 8, 7, 6, 3, and 1. FIG. 8B shows a path through nodes 4, 6, 9, 3, and 1. FIG. 8C shows a path through nodes 2, 6, 8, 9, 7, 5, 3, and 1. The use of the angles for distance measurements is useful given the three-dimensional nature of how the nodes and branches are arranged in a subject.

Exemplary Catheter Detection Embodiments

Further, in one embodiment, as part of the preprocessing of the angiography images, catheter detection is performed 160f. The presence of the catheter in the field of view may interfere with various steps and processing stages of a co-registration method. An intersection between the catheter and the vessel may be interpreted as a false bifurcation, which can lead to unstable tracking. Tracking of markers and centerlines can be negatively affected by the presence of the catheter delivering the intravascular imaging device. Another problem associated with such a catheter is that the shortest path between two points along the vessel may be passed through the catheter, instead of the vessel. As a result, the catheter can lead to error and false centerline generation.

Figure 9B:
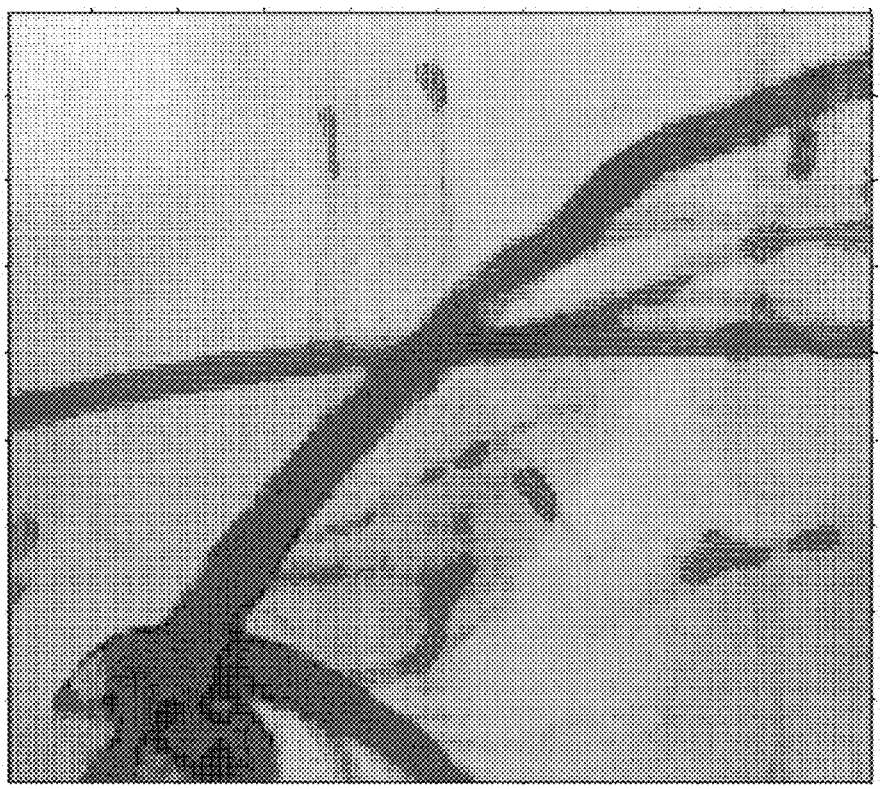
FIGS. 9A-9E show various image processing stages relating to catheter detection and removal in accordance with an illustrative embodiment of the invention.
Figure 9A:
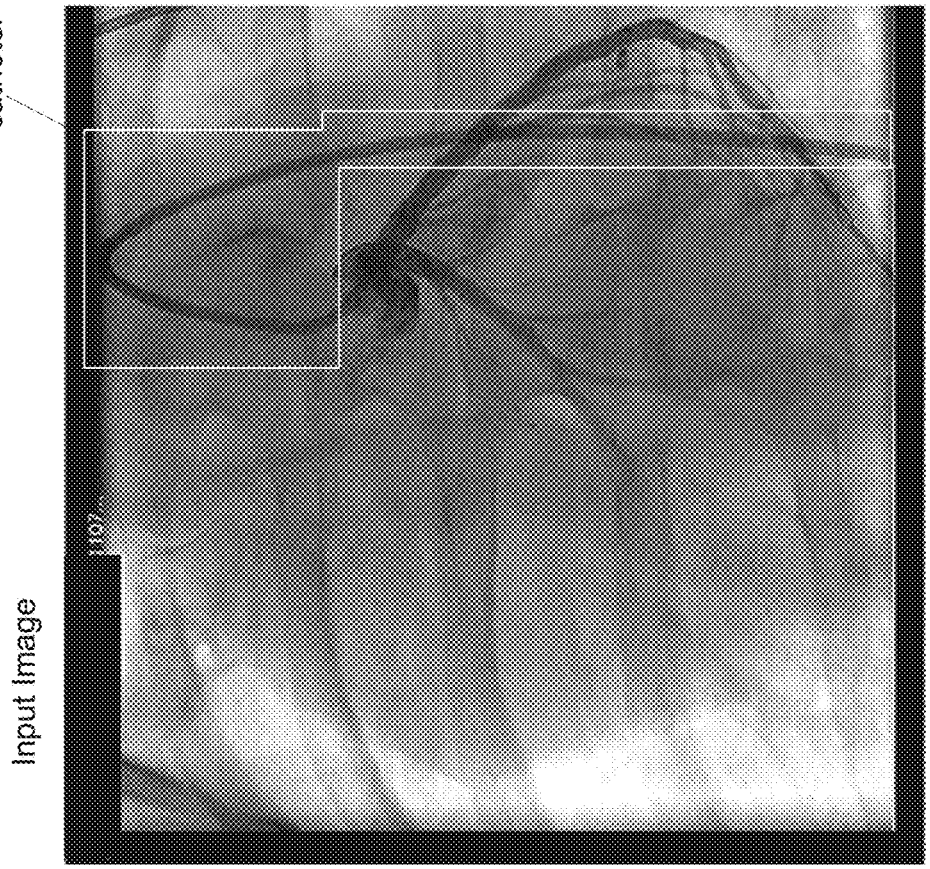
Figure 9D:
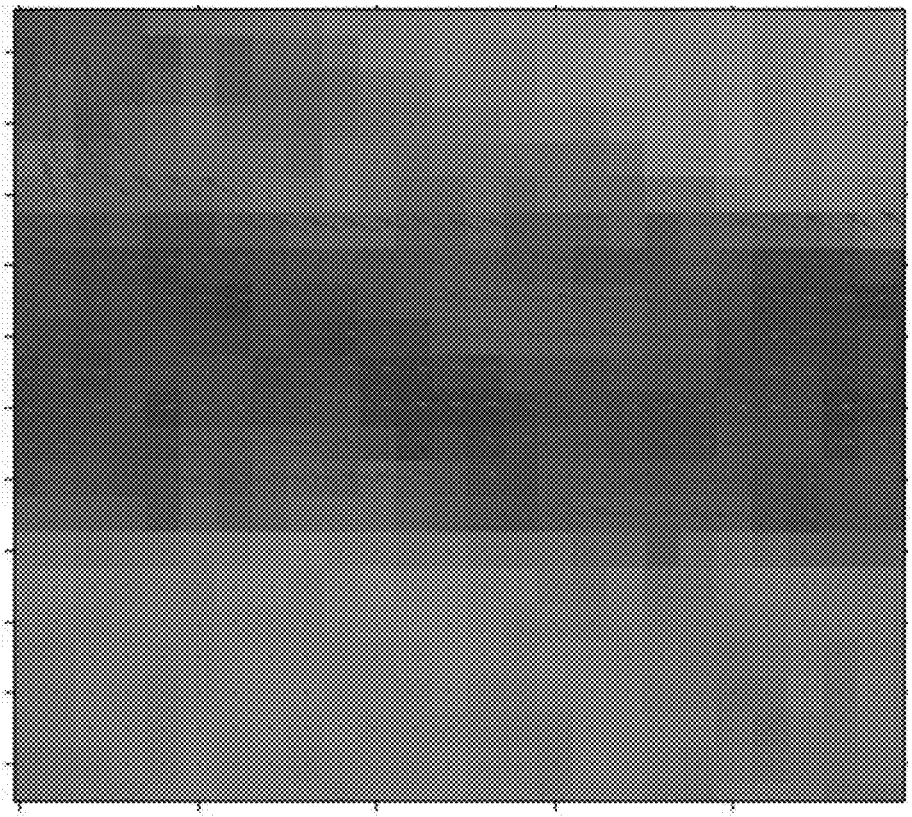
Figure 9C:
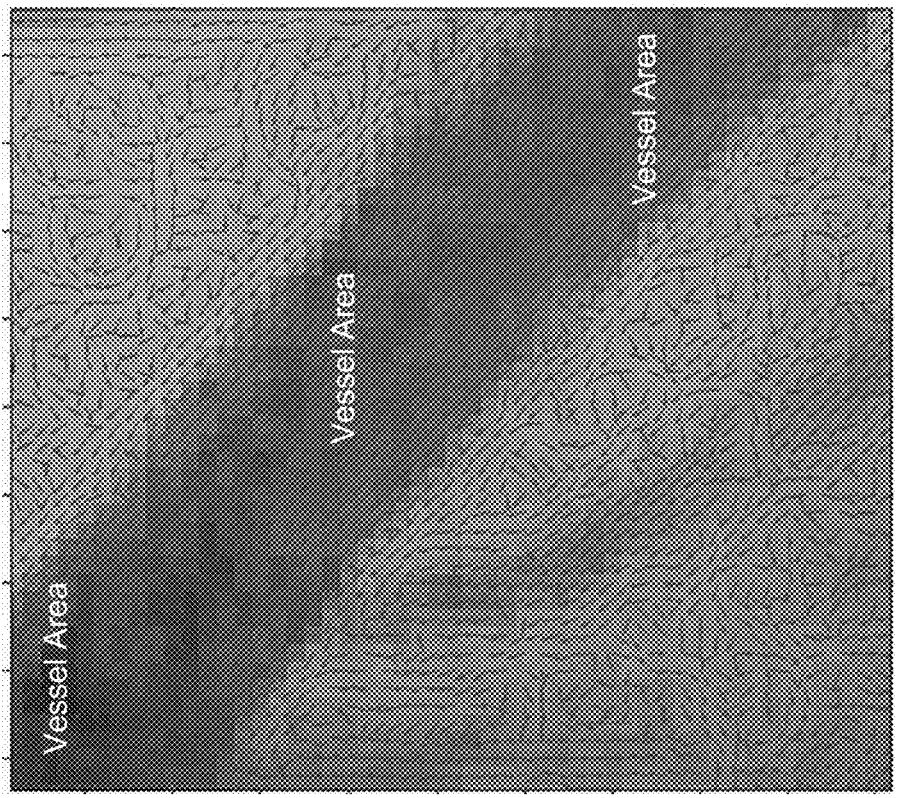

Therefore, it is desirable to be able to remove the catheter from each frame of angiography data prior to pursuing subsequent processing and detection such as in support of centerline generation. With respect to a given input angiography image, such as shown in FIG. 9A, a vector field such as shown in FIGS. 9B-9D can be superimposed on the image based on the detection of which sections of the image are moving and which sections of the image exhibit a directional field as shown in FIG. 9B with the catheter spanning the middle portion of the figure and the blood vessel crossing it at an angle roughly in the middle of the figure. FIG. 9C shows a vector field map of a vessel area while FIG. 9D shows the substantially straight and vertically directed vectors in the catheter area.

The vectors in the vector field illustrated in FIGS. 9C and 9D are the eigenvectors corresponding to the eigenvalues of the Hessian matrix computed by local second order analysis. In FIG. 9C, all the scales from 1 to 5 were used in a Frangi Filter. An example of such a filter is described in A. F.

Frangi, W. J. Niessen, K. L. Vincken, M. A. Viergever, "Multiscale vessel enhancement filtering", MICCAI'98, pp. 130-137, and thus the turbulent influences outside the vessel. In FIG. 9D, only scale sigma=4 was used and thus the isolated orientation on the catheter, while in the outer regions, the eigenvectors have zero weights. With regard to the sigma parameter, this parameter represents the scale of the Gaussian used in the convolution computation. Sigma=4 reflects the typical width in pixels for the catheter, as observed in the angiography dataset.

In one embodiment, catheter detection is based on a primary assumption of directionality of the catheter and on the fact that the catheter always intersects the lower boundary of the image such as shown in FIG. 9D. Though locally, the catheter and the vessel are generally not distinguishable from each other given their tubular structure. In terms of the shape of the catheter, the catheter can be differentiated from the vessel globally because it crosses almost the entire image and has a substantially straight shape. In one embodiment, the vector orientations are used to distinguish catheter and vessel. Locally, vessels may have small regions of orientation similar to the orientation of the catheter. The eigenvectors orientations of the catheter are in general closed to 90 degrees, while those of the vessels are not.

In one embodiment, a method of catheter detection is used that incorporate a Frangi filter for vesselness as well as for shape features. In one embodiment, the method includes determining at one scale only (sigma=4 which reflects the typical width in pixels of the catheter, as observed in the angiography dataset) the vesselness measure image and direction image based on the eigenvectors of the Hessian image. The catheter in a given image frame of angiography data can be isolated using various criteria. These criteria include the direction (threshold of direction image), the length of the connected component containing the catheter (the length of catheter profile should be at least half of the maximum image dimension in x (or y).

Figure 9E:
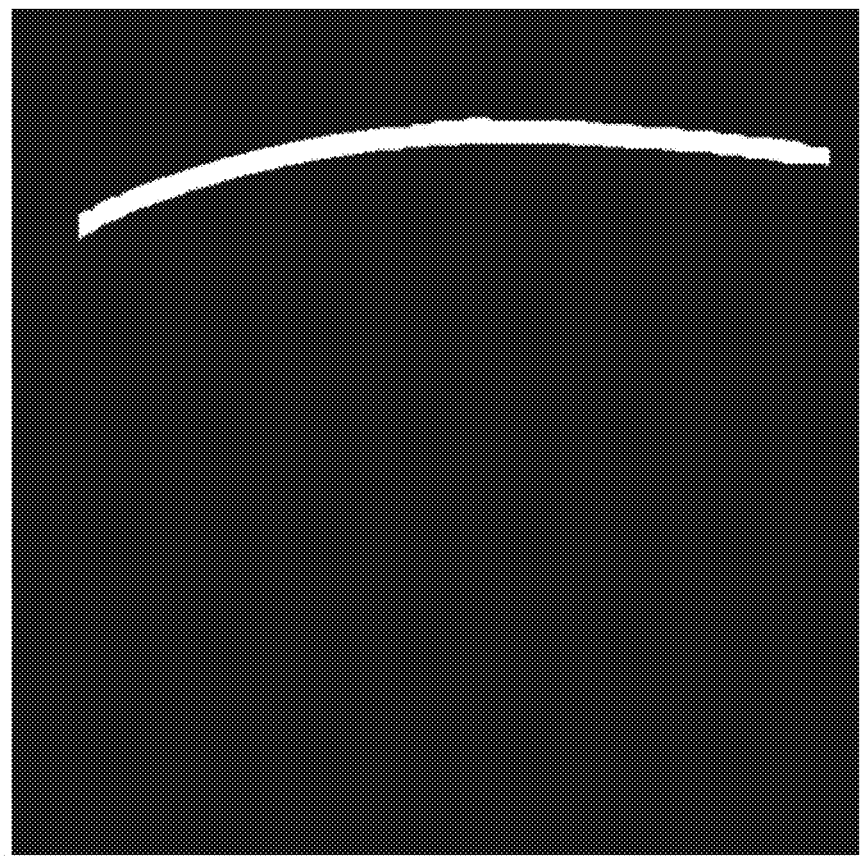

As a constraint for the image processing software, if the catheter is detected such that it appears in a given image, it is typically the case that the catheter crosses almost the whole image. In one embodiment, the system is programmed to assume the catheter always cuts the bottom boundary of the image. As a result, a lower bound can be set for the size of the detected object. In addition, once the regions of the angiography image associated with the catheter have been detected, it is useful to dilate or otherwise expand a boundary by a small increment around the centerline of the catheter to ensure a large enough feature has been detected. An example of a catheter detected based on the steps outlined above is shown in FIG. 9E.

Exemplary Catheter Removal Embodiments

As discussed above, the presence of the catheter in the field of view for a given angiography image may interfere with various steps and processing stages described herein. Accordingly, once the catheter has been detected such as by the software-based methods recited herein, it is desirable to remove the catheter. The bounded area in FIG. 9A shows the catheter overlapping a blood vessel at an angle. Various object elimination approaches for removing the catheter while still attempting to preserve the integrity of the image can be used. Based on a mask of the catheter, such as can be generated from or as an output of the catheter detection process used, a software module can be configured to remove the catheter mask by eliminating the catheter.

One advantageous approach to remove the catheter uses the principle of superpositioning of functions to cancel out and remove when out of phase relative to each other. In one embodiment, a superposition-based software module is used to perform catheter removal such as by estimating its intensity profile and reducing it from the image. A catheter intensity profile can be generated based upon sampling the points of the image identified as part of the catheter through a catheter detection software module.

Figure 10A:
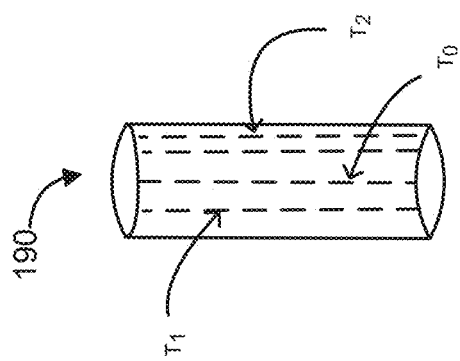
FIGS. 10A-10B show an exemplary model of a catheter and the effect of contrast solution it its intensity profile in accordance with an illustrative embodiment of the invention.
Figure 10B:
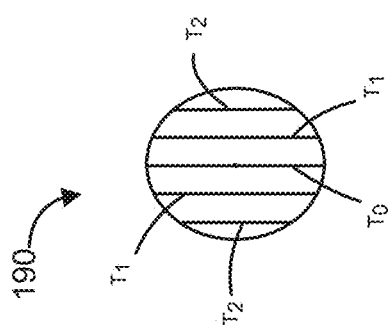
Figure 11A:
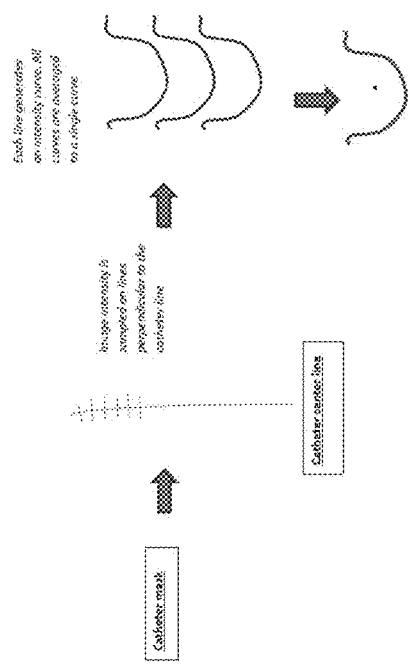
FIGS. 11A-11B show features of using a superposition based catheter removal method in accordance with an illustrative embodiment of the invention.
Figure 11B:
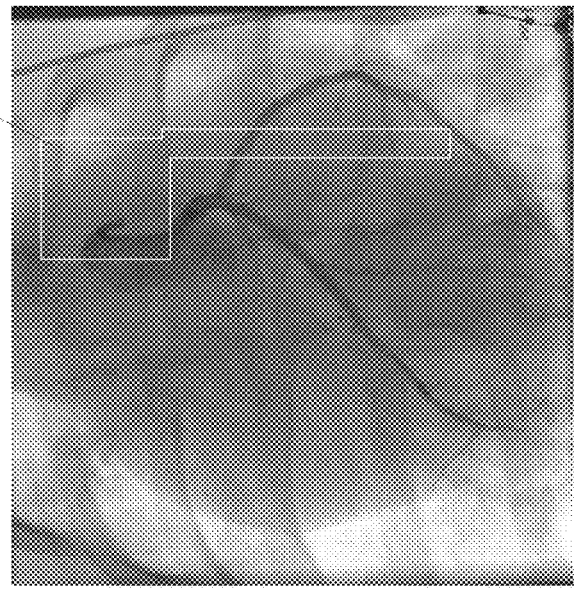

As shown in FIGS. 10A and 10B, an exemplary cylinder 190 is shown with various lengthwise slices of thickness T0, T1, and T2 as shown. The cylinder 190 can be viewed as a model representation of the catheter. To the extent the catheter and the cylinder 190 are filled with contrast solution the intensity changes caused by the contrast solution will be greater in the middle along thickness T0 and then decrease moving away from the center T0 to slice T1 and then further decrease as slice T2 is reached. Thus, as there is less contrast solution at the thinner edges of the catheter relative to the center of the catheter a profile of intensity for the catheter can be generated and added to the area of the image where the catheter was detected to remove the catheter from the image. An exemplary representation of a related catheter removal method is shown in FIG. 11A.

Given that the catheter has been detected as described herein, a mask associated with the pixels in the image that make up the catheter can be generated such as by using a mask region like that shown in FIG. 9E. In one embodiment, image intensity is sampled in the catheter region, such as for example, on lines perpendicular to the catheter line. These perpendicular lines span the gradient of contrast solution intensity changes that gradually decrease from one side of the catheter until a low or relative extremum is reached corresponding to the thickest middle portion of the catheter and then gradually increase again as the catheter cross-section thins at the edge of the catheter as show in FIGS. 10A and 10B. Each line sampled in the catheter area generates an intensity curve. The various intensity curves can be averaged to a single curve. This intensity curve can be inverted and then superimposed on the perpendicular lines that make up the catheter region to effectively remove the catheter from that region as shown in FIG. 11A.

Exemplary Shadow Removal Embodiments

The classical Hessian based filter is a part of the preprocessing and is based on the eigenvalues of the Hessian of the image. In one embodiment, the Hessian is computed at a number of discrete scales and then the maximum response among them is taken. In one embodiment of a shadow removal process, scales from 1 to 5 are used. Scale 5 can be chosen as the scale that best represents the maximum typical observed vessel width in the available data. Examples of original images and then processed to remove shadows and other features are shown in FIGS. 6I-6N.

The shadow removal preprocessing step is applied in order to transform an original image to a modified image having an improved contrast level. In addition, the modified images is changed by the process of applying the Hessian such that it is substantially free of the influence of the heart and diaphragm shadows which can induce several regions or planes of different contrasts. Removing these shadows is desirable because such regions or planes can lead to incorrect vessel centerlines. In one embodiment, the shadow removal step includes applying a bottom hat operator with a filter kernel configured to have a distance parameter that is much larger than the typical blood vessel width. FIGS. 6L and 6J show modified images that been improved by performing a shadow removal process.

Exemplary Vessel Centerline (Trace) Generation Embodiments

The two anchor points, distal and proximal, mark the end points and start point of the vessel centerline. The anchor points are reflected on the vessel skeleton and the Dijkstra algorithm is applied to find the shortest path in terms of smoothness. FMM is also applied to find a shortest path in terms of intensity (the FMM runs on the enhanced Hessian image). Results from the FMM are combined with Dijkstra result to produce the best vessel centerline (trace) between the two anchor points. Vessel centerlines in other angiography frames are generated by applying conformal mapping combined with FMM to the first generated trace.

In one embodiment, the fast marching technique or method deals with efficient computation of geodesic distances based on a potential. In one embodiment, when the contrast agent is present the potential can be the enhanced Hessian image. In one embodiment, when only the guidewire is present (even if visible on the angiography image in a piecewise manner), such as when no contrast agent is present, the potential is adjusted by constructing a function based on the distance transform. One method for the computation of the potential function the front will propagate on can be performed by a guidewire-based potential by applying a Euclidean distance transform on a binary image. Once the distance transform is generated such a transform can be further modified into a potential function by applying an exponent to a negative fractional power times the distance transform. An exemplary guidewire potential is shown in FIG. 6G.

Figure 5B:
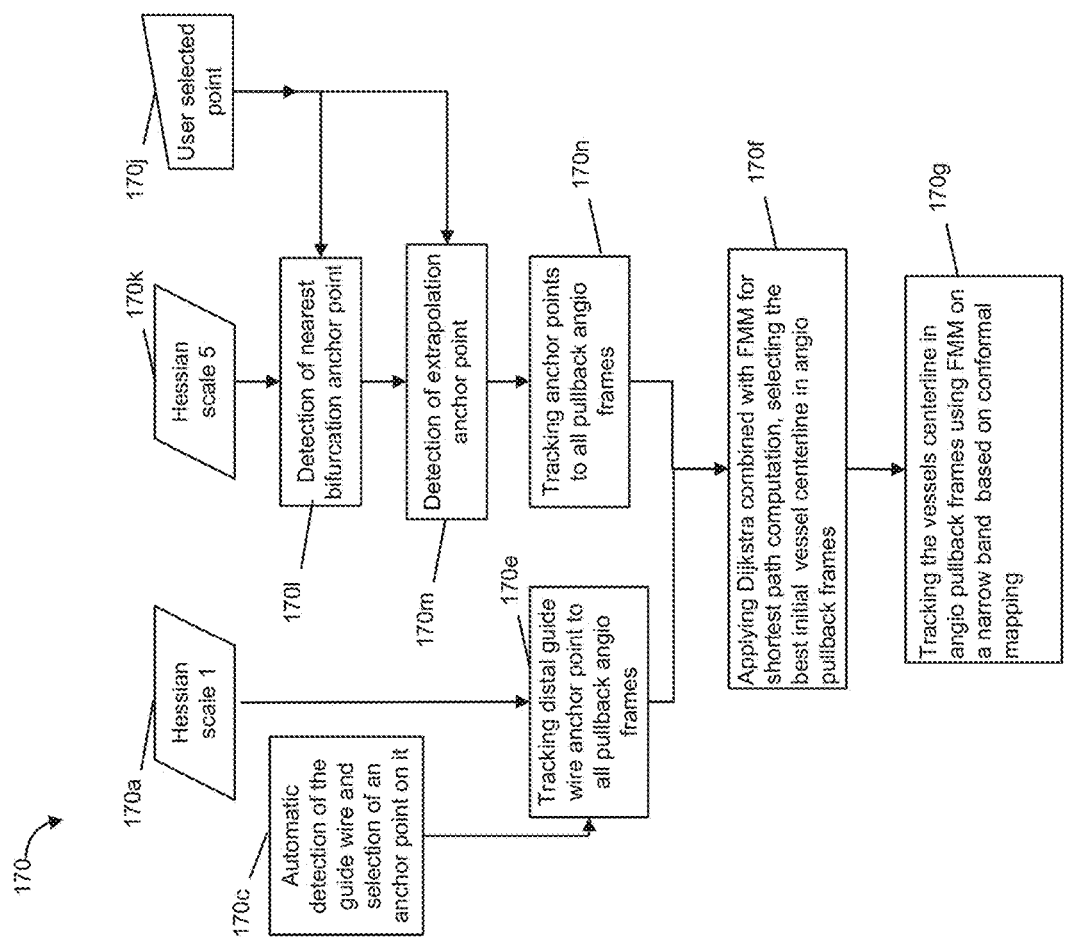
FIG. 5B shows a flow chart relating to some exemplary vessel centerline generation steps or stages in accordance with an illustrative embodiment of the invention.

FIG. 5B shows a process flow 170 relating to vessel centerline generation. In one embodiment, a Hessian having a scale of 1 is applied to a frame of angiography data 170a. This application of the Hessian results in enhancements of thin ridges in the image such as the guidewire. In one embodiment, automatic detection of the guidewire and selection of an anchor point on the guidewire is performed 170c. Once the guidewire is detected, in one embodiment, the point with the highest LoG response is identified as the anchor point. Tracking distal guidewire anchor point to all pullback angiography frames 170e is performed next. The proximal anchor point is detected in a single frame. The distal anchor point is also detected in a single frame. In one embodiment, each anchor point is a feature that can be easily detected in other frames by means of tracking. Next, anchor points are tracked to all frames so that each angiography frame will have two end points for vessel-centerline generation (trace).

In one embodiment, a user selected point such as a guidewire point on an angiography image is selected 170j. In turn, a Hessian of scale (up to about 5) can be applied 170k to an angiography image in order to enhance the vessels. The modified image as a result of the application of the Hessian can then be used to perform detection of nearest bifurcation anchor point 170l. This detection step can use the user selected point or hint point as an input. Next, detection of the extrapolation of an anchor point is performed 170m. Please clarify which anchor point is being detected. Next, tracking anchor points to all pullback angiography is performed frames 170n.

In one embodiment, the system next uses a graph search software module, such as a Dijkstra shortest path solution for a graph. Applying the Dijkstra algorithm or other shortest path algorithm combined with FMM and selecting a best initial vessel centerline can then be performed 170f with regard to the angiography pullback frames. Tracking the vessel centerline in angiography pullback frames using FMM on a narrow band based on conformal mapping is then performed 170g. In this context, narrow band means building a narrow band region around the trace of interest. This narrow band is intended to increase the efficiency of the FMM algorithm, due to computation of geodesic distances on a restricted region of the image. These centerlines can be stored in one or more tables and displayed on the applicable angiography images.

Exemplary Marker Detection and Co-Registration Embodiments

Figure 5C:
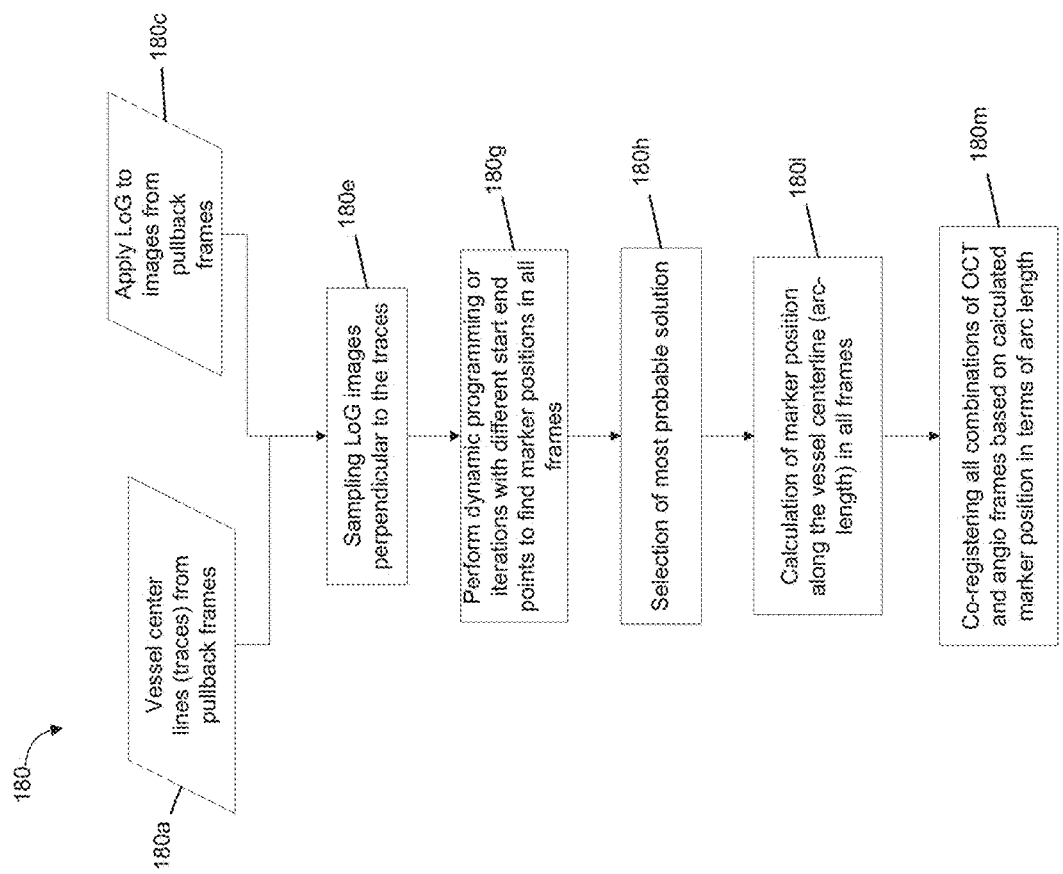
FIG. 5C shows a flow chart relating to some exemplary marker detection and co-registration steps or stages in accordance with an illustrative embodiment of the invention.

FIG. 5C shows a process flow 180 relating to marker detection and co-registration. As used herein, the term trace can be interchangeable with centerline. Initially, as an input the vessel centerlines (traces) from the pullback frames are provided as an input for sampling orientation 180a. In addition, a LoG is applied to images from the pullback frames 180c. Sampling LoG images perpendicular to the traces is performed 180e. In one embodiment, dynamic programming is performed or iterations are run with different starting or ending points to find marker positions in all frames 180g. In one embodiment, the dynamic programming or iterative process can be implemented using the Viterbi algorithm. Next, a selection of the most probable solution for a marker on a per frame basis is performed 180h. Calculation of marker position along with the marker normalized arc-length position along the vessel centerline in all frames is performed 180l.

Next, co-registering of all combinations of OCT and angiography frames based on calculated marker position in terms of arc length can be performed. Since all vessel centerlines start and end at the same anatomical features in all angiography frames, each centerline corresponds to the other centerlines in other frames. Therefore, centerline length or arc-length can be used as a basis for co-registration. The marker position in terms of arc length is preserved (up to some error) in all frames.

One challenge encountered when attempting to resolve the opaque marker bands of a sensor or data collection probe is the use of contrast solution as part of an OCT pullback. In one embodiment, it is useful to process frames of angiographic data prior to the introduction of contrast solution so that the guidewire and imaging catheter can be used to provide an initial path through the blood vessel. This initial dataset can be iteratively improved upon using other information and parameters as described herein.

A Viterbi based algorithm automatically detects the radiopaque marker in each image of the pullback. This algorithm can be used to obtain global solution based on blob intensity and predication of location (constant velocity along trace). As a prerequisite for this algorithm, a process of detecting and tracking the vessel centerlines (traces) is performed. The traces are used to create a continuous co-registration between the OCT and angiography. These curves are computed by means of the fast marching method. The fast marching method allows, on each frame, efficient computation of paths (traces) between the proximal point (which can be the user selected point or hint point) and the distal stationary marker. The stationary marker is detected on a frame (with and/or without contrast agent/dye). Template matching technique is employed to track both the proximal point and the distal marker over the subsequent sequence.

The Viterbi algorithm is configured to balance an extrinsic factor and an intrinsic factor. The extrinsic factor (marker band indications) is derived from the marker band Laplacian of the Gaussian map by resampling the map in discrete strips perpendicular to the trace, per angiography frame. The intrinsic factor is the arc-length progression over time. This intrinsic factor models the advancement of the marker band along the pullback's arc length. The basic notion is that the average pace is determined by the pullback speed, while there are penalties for deviating from this pace. This factor takes the natural "sawing" profile into account, by penalizing forward/backward motion differently.

Figure 12:
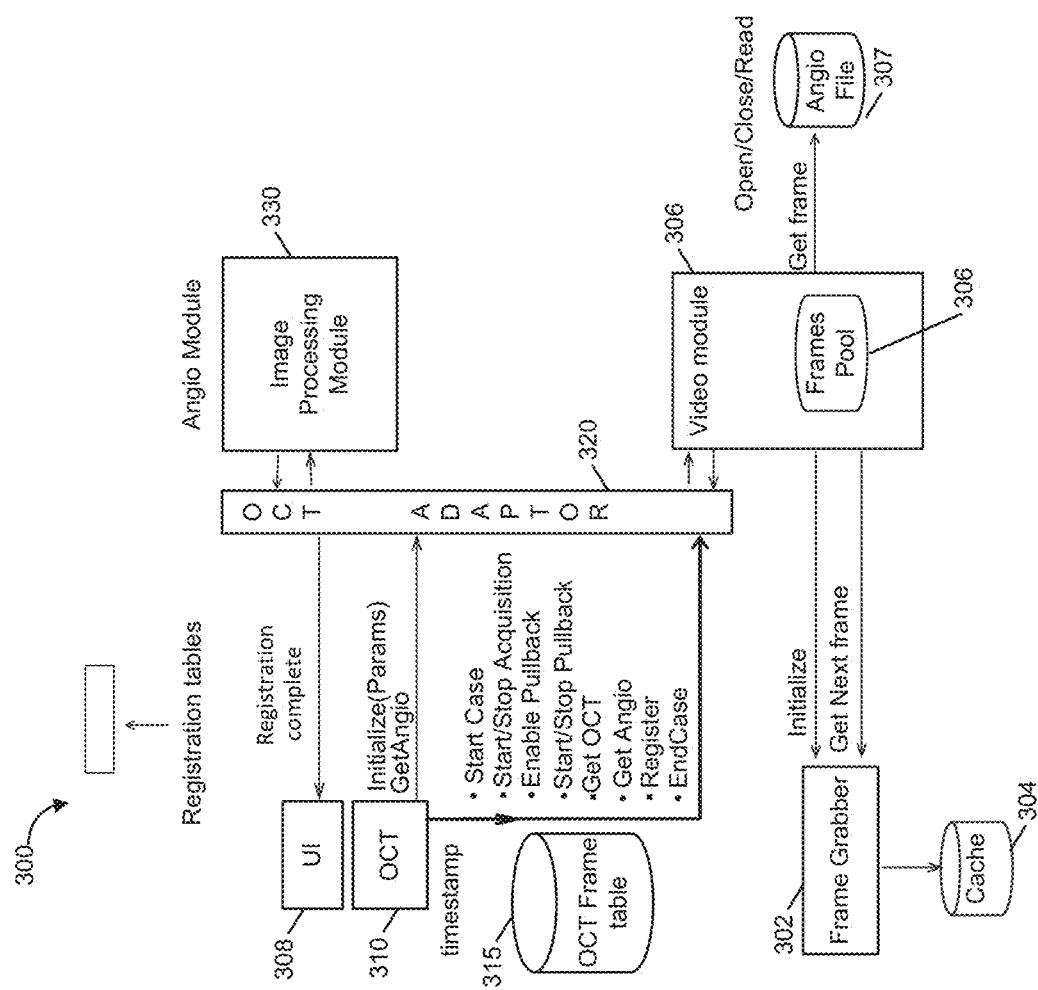
FIG. 12 shows a schematic diagram of various software and hardware components suitable for processing intravascular and angiographic image data in accordance with an illustrative embodiment of the invention.
Figure 13B:
FIGS. 13A and 13B show a schematic diagram of exemplary OCT and angiography data tables for a pullback in accordance with an illustrative embodiment of the invention.
Figure 13A:

FIG. 12 shows a data collection and co-registration system 300 that includes various software and hardware components suitable for processing intravascular and angiographic image data. In one embodiment, once one or more frames of OCT image data and angiography image data are co-registered the output is a registration table. In one embodiment, frame of OCT data can be monitored to check for clear frame indication state and this clear frame indication can be used to trigger the Cine such that the frames of angiography data can be captured. In one embodiment, for a given pullback procedure during which a probe is pull backed through a blood vessel while probe data and angiography data are collected, time stamping of frames, registration table population, and image processing features, and other processes may be performed.

The user interface (UI) 308 is in communication with the OCT adaptor 320. The Image Processing Module 330 is in communication with the OCT adaptor 320. In one embodiment, the image processing module 330 performs or applies operators or transforms to frames of angiography data such as for shadow removal, guidewire detection, catheter removal, and other image processing steps outlined herein. The optical coherence tomography system 310 is in communication with the OCT adaptor 320. The optical coherence tomography system 310 can include or be in communication with the framer grabber 302. Angiography frames are grabbed using the frame grabber and fetched by the software module.

The OCT frame table 315 includes information and images of a blood vessel obtained during a pullback of an imaging probe through the blood vessel. The role of the OCT adaptor 320 is provide a software interface between the angiography system and the OCT system.

The software-based systems, such as the server or workstation described herein, and the software modules configured to automatically run and capture the angiography images and tag each image by its acquisition time support co-registration of intravascular data tagged with an acquisition time. The image processing module 330 which can include a co-registration software module automatically detects the radio-opaque marker on each angiography image corresponding to the intravascular acquisition. A single user input may be requested to assist with the detection as shown in FIG. 5B. The co-registration software module computes the intravascular imaging catheter's path on all angiography images corresponding to the intravascular image acquisition during the pullback of the probe through the vessel being imaged. The co-registration software module produces a co-registration table of the acquisition's intravascular and external images that include the radio-opaque marker's location on each angiography image; position of each intravascular image/data point on each angiography image; and a FOM associated with each co-registration result, providing a measure of the level of confidence in the veracity of that result.

The user is presented with graphic representations of the intravascular and angiographic images, and with the correspondence between the two, such as location of a certain intravascular image on the angiographic image as part of a user interface when co-registration is complete in one embodiment. If during a co-registration procedure a FOM or confidence score is not acceptable, additional user input or other parameters from the OCT system may be requested or automatically obtained.

Exemplary Confidence Score/Figure of Merit Embodiments

For each detection of a probe marker a confidence score also referred to as a FOM assigned to each detected probe marker. Score is based on one or more of blob intensity, the number of dark blobs in the vicinity of the predicted area of the marker, the marker arc-length along the traces, the blob movement, and the stability of traces. The FOM/Score reflects a confidence measure in the returned results. In one embodiment, the score is in the range [0, 1] where 0 reflects the lowest confidence and 1 reflects the highest.

The angiography related software modules, such as one or more modules described herein, are evaluating images generated using imaging devices that are typically disposed outside of a subject's body. In contrast, a data collection probe, such as an OCT, IVUS, FFR, pressure, or other data collection modality, can be disposed within the blood vessel of a patient. As a result, data obtained from such a data collection probe during a pullback or previously known as a data collection probe relating parameter can be used by the angiography software to improve the operation of the methods and stages described herein. An adapter software module or other software module can be used to provide OCT information to the angiography image frame processing software modules and vice versa.

For example, the following parameters relating to data obtained with regard to a blood vessel as part of the intravascular data collection, can be transmitted to the angiography software or other software modules for analysis or to otherwise help evaluate the subject or otherwise relate different datasets, pullback length in mm, start of pullback, end of pullback, indications of bifurcations such as side branches from collected OCT data, data collected with regard to frames prior to the introduction of a contrast agent or dye, OCT and angiography synchronized frames timetags, pullback velocity, distance between the distal and the proximal markers of the catheter and other factors and parameters obtained with respect to a given data collection modality such as longitudinal blood vessel image data, pressure data, EKG data, systole state during pullback, diastole state during pullback, and other information available relating to a subject.

Angiography Table

Figure 14:
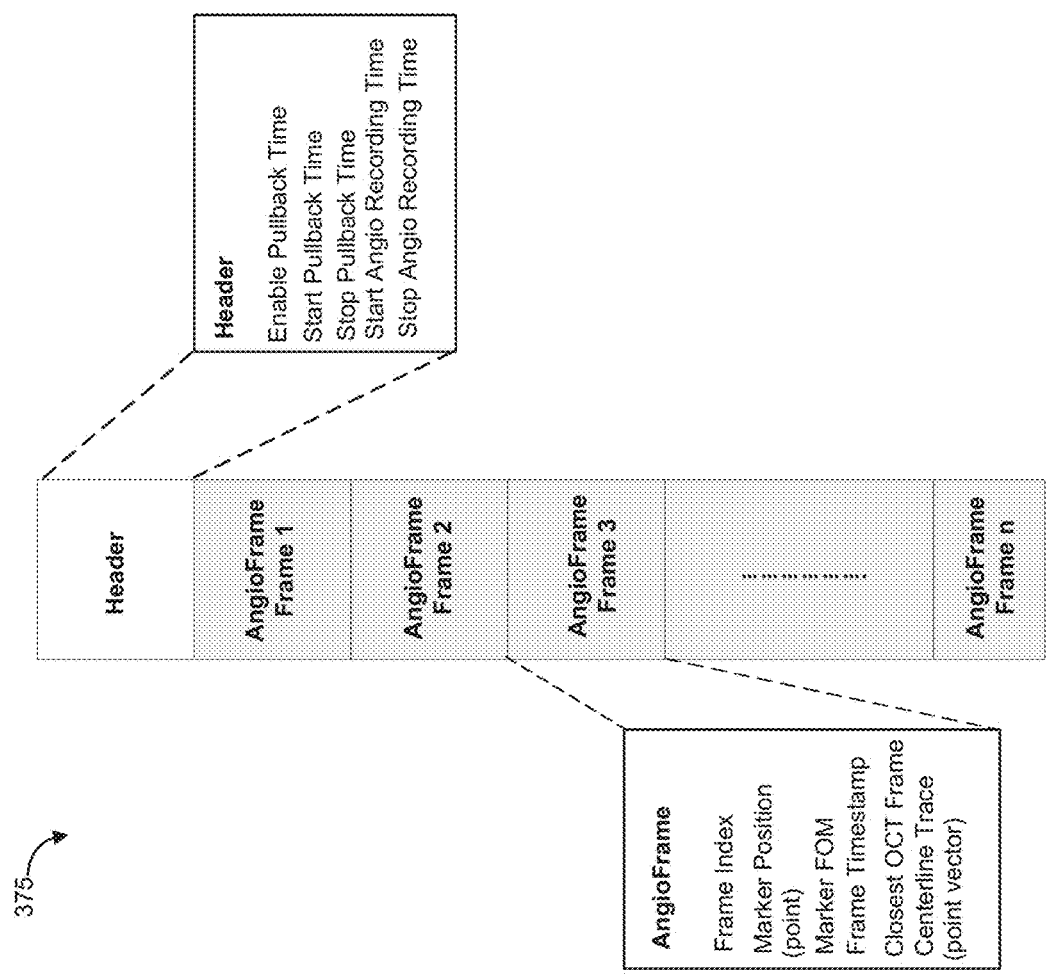
FIG. 14 shows a schematic diagram of an exemplary angiography data table for a pullback in accordance with an illustrative embodiment of the invention.

The angiography table, such as shown in FIG. 14, contains information that describes the angiography pullback as well as each angiography frame acquired. The angiography table is created by the angiography software module at acquisition and is partially populated with time stamp data. This table is extracted by the OCT module at the completion of acquisition and stored. The table is then provided to the angiography software module at co-registration time, when the co-registration dependent fields are populated.

Co-Registration Table

Figure 15:
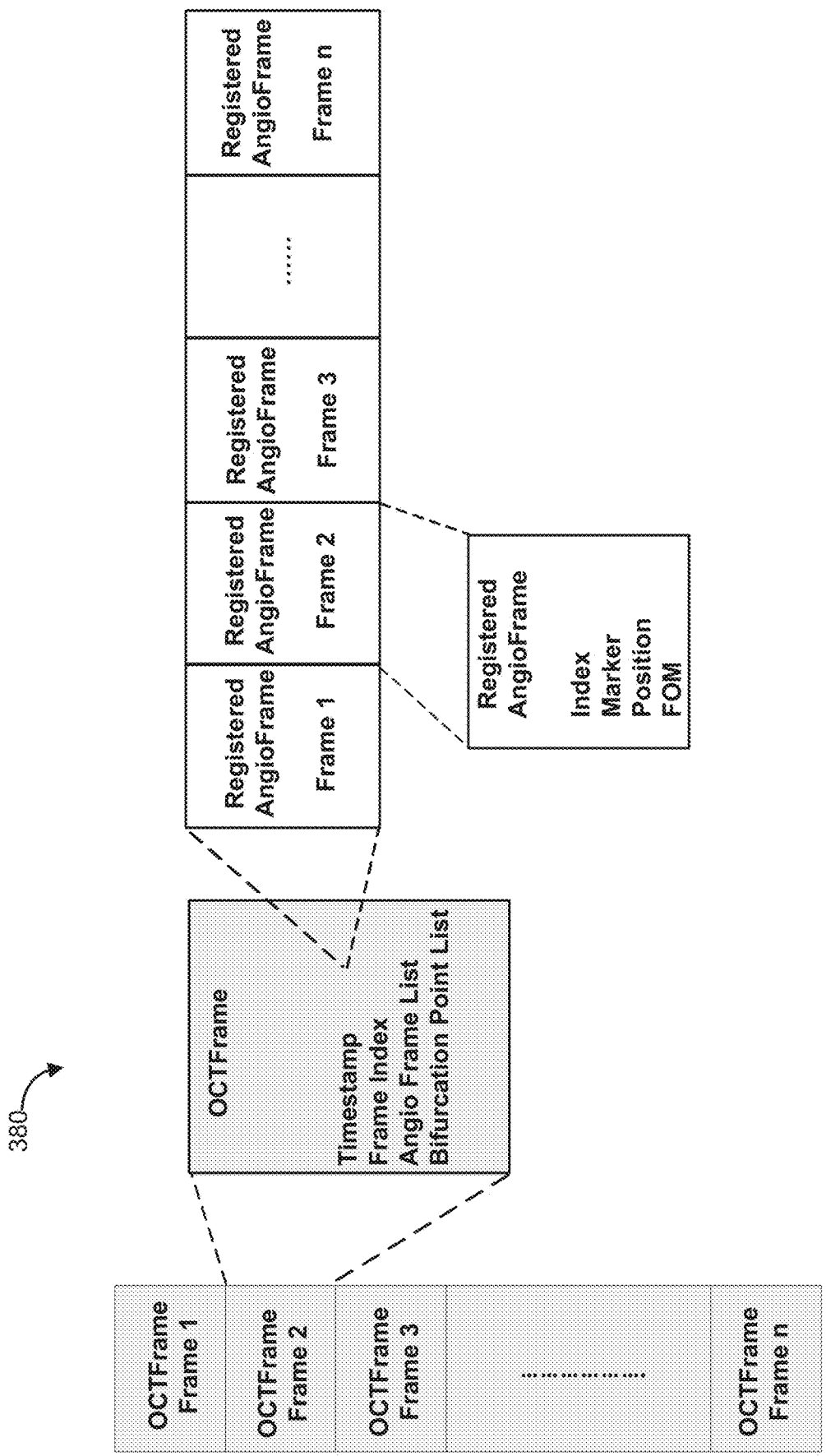
FIG. 15 shows a schematic diagram of an exemplary co-registration table in accordance with an illustrative embodiment of the invention.

The co-registration table contains the results of a successful co-registration as shown in FIG. 15. It contains all of the OCT/angiography cross-reference information necessary to drive the co-registration GUI toolset. This table contains an entry for each OCT frame which contains that frame's acquisition time stamp and a list with an entry for each angiography frame containing the OCT marker position information. In one embodiment, the co-registration table associates the OCT frame index with the registered angiography frame index. Additionally, the table can include an entry which associates an OCT frame and angiography frame.

Additional Multimodal Co-Registration Features and Embodiments

In one embodiment, co-registration refers to synchronizing frames from two or more data collection modalities or otherwise combining information from two or more data collection modalities. For example, bifurcations detected on OCT images can be used as anchors with respect to bifurcations detected on angiography images. The co-registration features recited here are not limited to OCT. Instead, the features described here relating to co-registering imaging or other data collection modalities relating to the vascular system and individual blood vessels can be extended to other intravascular imaging modalities. In one embodiment of the invention, the centerline of the vessel is determined from the path of a guidewire or catheter that is tracked by a tracking system such as the Medical Position System of Mediguide during its advancement through the vessel.

In one embodiment, side branches detected in OCT frames of data using OCT image processing can be used as an input to improve co-registration with angiography data. For example, in one embodiment, each OCT frame includes a flag (yes/no) indicating if a sidebranch is present. Further, once the co-registration is obtained, positions of stents, calcium deposits, lipid deposits, thrombus, thin capped fibroatheromas (TCFAs or "vulnerable plaques"), vessel normalization, side branch detection, FFR values (which may be computed as a vascular resistance ratio (VRR) values based on OCT image data), lumen size values, stents, and various other data described herein can be overlaid on the angiography image or the OCT images in light of the co-registration between the datasets.

Live Stent Placement Guidance Embodiments and Features

In one embodiment, following OCT/angiography co-registration, the guidewire is retained post-pullback for stent placement via another catheter. The process of imaging the blood vessel that was the subject of the pullback continues via continued fluoroscopic imaging, co-registered to OCT. Moving along the OCT frames or angiography frames allows side branches and other information to be seen. In one embodiment, various processing steps are performed with regard to the OCT data such as detection of prior stents, 3-D co-registered virtual histology, lumen detection, guidewire detection, stent malapposition, plaque detection, and others. Since the OCT and angiography frames are registered, information found in the OCT frames can be overlaid on the angiography screen that the operator will use to place a stent. If side branches can be shown in the angiography view on a user interface, this can help avoid the unwanted caging of a side branch during stent deployment.

In addition, various types of overlays relating to stents that have been previously deployed or that are candidates for deployment can be displayed on one or both of an OCT image and angiography image following co-registration. For example, bioresorbable vascular scafford (BVS), a new type of stent that is radio-translucent, can be detected on OCT frames using OCT image processing. This OCT image data can be used to provide a specific type of stent overlay that is important in the context of the angiography data because such stents are not made visible by x-rays. As another special case of data overlay, in one embodiment, stent malapposition information from a given OCT frame can be used to color code or generate other indicia to modify the stent image on the X-ray image to show regions of malapposition.

In addition, given that a marker on the stent delivery probe can be tracked, a stimulated stent can be shown in relation to the marker on the OCT longitudinal mode or L-mode. The angiography/OCT co-registration allows cross-correlating of tissue features, lumen features and moving features such as a balloon or stent insertion to be shown in the angiography with overlays and with the display of elements such as a stent cross-section in the L-mode. If a scan of the stent is obtained as a wireframe model or is selected from a drop down menu prior to stenting, the diameter and length can be used to display the stent on the L-mode or angiography with greater accuracy.

In one embodiment, bands on the OCT image and/or the angiography image showing regions to avoid stenting like side branches and a target deployment region based on stenosis/MLA calculations can be used. The angiography and OCT displays can be used to show a greater level of granularity with overlays to help a user properly position a stent within a target area. In addition, given the wireframe model of the stent and the calculated lumen areas from the OCT frames that are co-registered with the location of the stent on the angiography system, visual guidance for a stent inflation target can be provided and displayed. In one embodiment, this can be performed using a simulated wireframe of the stent and the expanding balloon used to selectively expand one or both ends of the stent. These types of investigations using OCT and angiography can be used on a pre-stent, post-stent, or as part of future follow ups.

In one embodiment, when a pullback is performed the OCT data and angiography data are stored. This stored data can be used to generate images or a model of an artery. With such a model, live stent placement during a subsequent pullback is enhanced. In this way, the prior existing OCT/angiography co-registration information can be used as a baseline.

Angiography data can also be used to inform or improve or correct OCT image display features or detection algorithms. One correction in OCT from angiography data is to re-space the OCT frames on the L-mode to show the actual, physical separation between frames as measured by the co-registration tool. This compensates for spacing errors that arise from assuming a constant pullback velocity relative to the vessel lumen. In reality the pullback velocity varies significantly due to cardiac motion and our frames are not equally spaced. A software module can be used to measure the frame-to-frame spacing accurately once co-registered OCT and angiography datasets are generated. A per frame correction can be applied to re-space the L-mode view in a given user interface. This can also be applied to 3D OCT renderings, which would provide a more accurate visual representation of the vessel.

In general, by having a co-registered set of frames and bidirectional communication between angiography and OCT systems, various additional benefits are possible. The angiography information includes traces that have been generated for different vessels. The junctions of these branches can be mapped to particular frames to inform OCT side branch detection. In one embodiment, by storing angiography data and OCT obtained during angiography, a record can be built over time that can be used to co-register OCT images at different time points with the angiography data acting as a bridge or linker between two different OCT datasets.

In one embodiment, a pressure probe or other data collection modality can be used to collect data to improve the representation of a blood vessel using another imaging modality or parameters. In one embodiment, VRR can be used to calculate the percentage contribution of each stenosis to an overall FFR value and display the relative percentages on the angiography image. In addition, side branch position information from the OCT images or the angiography images can be used to improve VRR calculation by identifying additional junctions and points of flow in the area near a blood vessel being imaged.

In one embodiment, the system and methods can be used to monitor a thrombectomy catheter in OCT L-mode: This can be used with guided stenting using simulated stents and registration data as described herein. In general, in part the invention relates to the tracking of any therapeutic device with a radio-opaque marker band, and displaying its position on the OCT L-mode and the previously-acquired co-registered X-ray images. The therapeutic device can be a stent or a thrombectomy catheter, or a balloon device such as an angioplasty balloon or dug-eluting balloon, or an excisional device such as a rotational atherectomy probe (Rotablator). Non-Limiting Software Features and Embodiments for Implementing Angiography and Intravascular Data Collection Methods and Systems The following description is intended to provide an overview of device hardware and other operating components suitable for performing the methods of the invention described herein. This description is not intended to limit the applicable environments or the scope of the invention. Similarly, the hardware and other operating components may be suitable as part of the apparatuses described above. The invention can be practiced with other system configurations, including personal computers, multiprocessor systems, microprocessor-based or programmable electronic devices, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "calculating" or "comparing" or "arc length measuring" or "detecting" or "tracing" or "masking" or "sampling" or "operating" or "generating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention, in some embodiments, also relates to the apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the invention may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe, an FFR probe, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, performing image procession using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as angiography data, OCT data, FFR data, IVUS data, co-registration table data, centerlines, shadows, pixels, intensity patterns, and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It should be appreciated that various aspects of the claimed invention are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Accordingly, what is desired to be secured by Letters Patent is the invention as defined and differentiated in the following claims, including all equivalents.

What is claimed is:

1. A method of co-registering angiographic data and intravascular data obtained with regard to a blood vessel comprising storing a plurality of frames of intravascular image data in memory;
   storing a plurality of frames of angiography image data in memory;
   substantially reducing or removing one or more shadows, using one or more computing devices, in the plurality of frames of angiography image data;
   removing a guide catheter image from one or more frames of angiography image data using superposition of an intensity profile;
   generating a vessel trace for each frame of the plurality of frames of angiography image data, using the one or more computing devices;
   detecting a probe marker in the plurality of frames of angiography image data, using the one or more computing devices; and
   tracking a position of the probe marker along one or more vessel traces, using the one or more computing devices.

2. The method of claim 1 further comprising co-registering the plurality of frames of angiography image data and the plurality of frames of intravascular data using the tracked position of the probe marker relative to one or more vessel traces.

3. The method of claim 1 further comprising:
   detecting a catheter in the plurality of frames of angiography image data, using the one or more computing devices; and
   removing the detected catheter from the plurality of frames of angiography image data, using the one or more computing devices.

4. The method of claim 3 wherein removing the detected catheter is performed using superposition of an intensity profile generated based on a sampling of regions of the detected catheter.

5. The method of claim 1 wherein the one or more shadows are selected from the group consisting of a cardiac shadow and a diaphragm shadow.

6. The method of claim 1 further comprising applying an image processing transform to one or more frames of angiography image data to remove or modify a feature therein and increasing an intensity of a plurality of pixels, the plurality of pixels corresponding to the probe marker or a guidewire.

7. The method of claim 1 further comprising generating a score indicative of a level of confidence in co-registration between a frame of angiography image data and a frame of the intravascular data.

8. The method of claim 1 wherein each vessel trace is a curve along the blood vessel that includes a proximal point and a distal point, wherein the distal point is the detected marker.

9. The method of claim 1 wherein the step of co registering the plurality of frames of angiography image data and the plurality of frames of intravascular data comprises generating a co-registration table, using a computing device, the co-registration table comprising angiography image data frames, a plurality of per frame intravascular data time stamps, a plurality of per frame angiography data time stamps, and intravascular image data frames.

10. The method of claim 1 further comprising displaying a stent representation in an intravascular image and an angiography image in a user interface using a co-registration table and a computing device.

11. The method of claim 1 wherein detecting a probe marker comprises identifying probe marker candidates by identifying a relative maximum in a neighborhood of pixels.

12. The method of claim 1 wherein the step of generating a vessel trace comprises applying one or more image processing operators to each angiography image data frame and applying a fast marching method relative to a first point and a second point in each frame.

13. The method of claim 1 further comprising applying a bottom hat operator to one or more frames of angiography image data and applying a morphological close operation to the one or more frames of angiography image data.

14. The method of claim 1 further comprising generating a confidence score for each detection and co-registration between angiography image data and intravascular image data.

15. The method of claim 1 further comprising performing a morphological image reconstruction for each probe marker candidate.

16. The method of claim 1 wherein tracking a position of the probe marker is performed using template matching.

17. The method of claim 1 wherein tracking a position of the probe marker is performed using a Viterbi dynamic programming method.

18. A method of co-registering angiographic data and intravascular data obtained with regard to a blood vessel comprising storing a plurality of frames of intravascular image data in memory;
   storing a plurality of frames of angiography image data in memory;
   substantially reducing or removing one or more shadows, using one or more computing devices, in the plurality of frames of angiography image data;
   generating a vessel trace for each frame of the plurality of frames of angiography image data, using the one or more computing devices;
   detecting a probe marker in the plurality of frames of angiography image data, using the one or more computing devices;
   tracking a position of the probe marker along one or more vessel traces, using the one or more computing devices; and
   co-registering the optical coherence tomography data and the angiography data using vessel traces to create a continuous registration of a tracked marker, and displaying two or more co-registered angiography images and optical coherence tomography images, wherein the intravascular data is optical coherence tomography data, wherein the probe marker is attached to an intravascular optical coherence tomography probe.

19. A method of co-registering angiographic data and intravascular data obtained with regard to a blood vessel comprising:
   storing a plurality of frames of intravascular image data in memory;
   acquiring, using a frame grabber, time stamped frames of angiography image data;
   storing a plurality of the time stamped frames of angiography image data in memory;
   substantially reducing or removing one or more shadows, using one or more computing devices, in the plurality of frames of angiography image data;
   generating a vessel trace for each frame of the plurality of frames of angiography image data, using the one or more computing devices;

detecting a probe marker in the plurality of frames of angiography image data, using the one or more computing devices; and tracking a position of the probe marker along one or more vessel traces, using the one or more computing devices.

* * * * *